(12) United States Patent
Nakagawa et al.

(10) Patent No.: US 8,168,827 B2
(45) Date of Patent: May 1, 2012

(54) AMIDE DERIVATIVE

(75) Inventors: Tadakiyo Nakagawa, Kawasaki (JP);
Tamotsu Suzuki, Kawasaki (JP); Kaoru Takenaka, Kawasaki (JP); Shinichi Fujita, Kawasaki (JP); Youji Yamada, Kawasaki (JP); Yoichiro Shima, Kawasaki (JP); Tatsuya Okuzumi, Kawasaki (JP); Toshihiko Yoshimura, Kawasaki (JP); Masanao Yoshida, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/487,813

(22) Filed: Jun. 19, 2009

(65) Prior Publication Data
US 2009/0258900 A1    Oct. 15, 2009

Related U.S. Application Data

(60) Division of application No. 11/281,627, filed on Nov. 18, 2005, now Pat. No. 7,572,815, which is a continuation of application No. PCT/JP2004/007221, filed on May 20, 2004.

(30) Foreign Application Priority Data

May 20, 2003   (JP) .................. 2003-142681

(51) Int. Cl.
*C07C 233/05* (2006.01)
*A61K 31/65* (2006.01)
(52) U.S. Cl. ........................ 564/188; 514/619
(58) Field of Classification Search .................. 564/188; 514/619
See application file for complete search history.

(56) References Cited

U.S. PATENT DOCUMENTS

| | | | |
|---|---|---|---|
| 3,663,529 A | | 5/1972 | Kubba et al. |
| 3,920,719 A | * | 11/1975 | Desai et al. .................. 558/397 |
| 5,442,064 A | | 8/1995 | Pieper et al. |
| 6,166,038 A | | 12/2000 | Fukami et al. |
| 2004/0077628 A1 | | 4/2004 | Ishihara et al. |
| 2004/0152690 A1 | | 8/2004 | Balan et al. |
| 2005/0009841 A1 | | 1/2005 | Zheng et al. |
| 2005/0080095 A1 | | 4/2005 | Zheng et al. |
| 2009/0143575 A1 | | 6/2009 | Balan et al. |

FOREIGN PATENT DOCUMENTS

| | | |
|---|---|---|
| CA | 2108093 | 4/1994 |
| CA | 2 407 149 A1 | 11/2001 |
| DE | 2017919 | * 11/1970 |
| EP | 0 945 439 A1 | 9/1999 |
| JP | 62-089679 | 4/1987 |
| JP | 6-199788 | 7/1994 |
| JP | 2002-88073 | 3/2002 |
| JP | 2005-526723 | 9/2005 |
| WO | WO 98/25908 | 6/1998 |
| WO | WO 00/27842 | 5/2000 |
| WO | WO 01/82925 | 11/2001 |
| WO | WO 02/08221 | 1/2002 |
| WO | WO 02/16317 | 2/2002 |
| WO | WO 02/16318 | 2/2002 |
| WO | WO 02/16319 | 2/2002 |
| WO | WO 02/20484 A1 | 3/2002 |
| WO | WO 02/28885 | 4/2002 |
| WO | WO 02/072536 | 9/2002 |
| WO | WO 02/076946 | 10/2002 |
| WO | WO 02/090326 | 11/2002 |
| WO | WO 03/022809 | 3/2003 |
| WO | WO 03/068749 | 8/2003 |
| WO | 2004/035549 | 4/2004 |
| WO | WO 2005/004866 | 1/2005 |
| WO | WO 2005/007642 | 1/2005 |

OTHER PUBLICATIONS

West, Anthony R., Solid State Chemistry and its Applications, Wiley, New York, 1988, pp. 358 & 365.*
Database Accession No. 265423, Database Beilstein, Beilstein Institute for Organic Chemistry, Frankfurt-Main, Germany, XP-002304637, *Coll. Czech. Chem. Commun.*, vol. 6, pp. 225-230 (1934).
Database Accession No. 2002:1865983, Publication Date: Jul. 9, 2002, Database CHEMCATS, Chemical Abstracts Service, Columbus, Ohio, XP-002304640.
Office Action issued Oct. 28, 2010, in Canada Patent Application No. 2,526,361.

(Continued)

*Primary Examiner* — Shailendra Kumar
(74) *Attorney, Agent, or Firm* — Oblon, Spivak, McClelland, Maier & Neustadt, L.L.P.

(57) ABSTRACT

Amide derivatives represented by the formula (I):

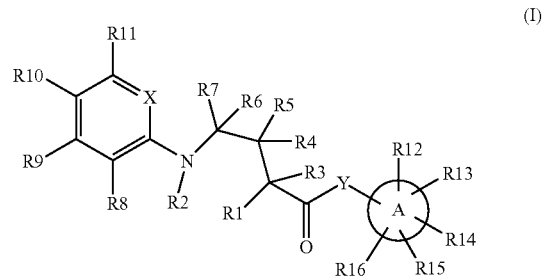

wherein:
A is a cycloalkyl group, an aryl group or a heteroaryl group; X is a nitrogen atom or CR17; Y is —NRa-, —(CRbRb') m-, and the like; m is 0 to 4; and R1 to R17 may be the same or different and each is a hydrogen atom, a halogen atom, a cyano group, a nitro group, a carboxyl group, a formyl group, a hydroxyl group, an ammonium group, an alkyl group optionally having one or more substituents, -ZR18 and the like, Z is —O—, —S(O)p-, —S(O) pO—, —NH—, —NR19-, and the like; or a pharmaceutically acceptable salt thereof, a hydrate thereof, or a solvate thereof may be applied to pharmaceutical use such as anti-inflammatory and analgesic action and the like.

13 Claims, 6 Drawing Sheets

OTHER PUBLICATIONS

Database CHEMCATS—Chemical Abstracts Service, Registry Nos. 110106-42-8: 110106-45-1: 110106-46-2: 110106-47-3: 309742-61-8: 337919-69-4: 309733-67-3: 265104-50-5: 372148-47-5: 404030-97-3: 405907-69-9: 209005-63-0: 198648-67-8: 209005-64-1: 209005-65-2: 209005-66-3: 198648-67-8: 162997-30-0: 162997-43-5: 110106-42-8: 110106-45-1: 69082-53-7: 69082-55-9: 69082-67-3: 69082-68-4, Dec. 3, 2010, 9 pages.

Office Action issued Jun. 20, 2011 in Canada Application No. 2,526,361.

Harold W. Heine, et al., "Aziridines. XIII. Reactions of 1,2,3-Triarylaziridines with Activated Alkenes and Alkynes", Journal of Organic Chemistry, vol. 31, 1966, pp. 3924-3927.

Pretrial Examination Report issued Nov. 11, 2011, in Japanese Patent Application No. 2011-022424 (with English-language Translation).

* cited by examiner

AMIDE DERIVATIVE

CROSS REFERENCES TO RELATED APPLICATIONS

This application is a division of U.S. patent application Ser. No. 11/281,627, now U.S. Pat. No. 7,572,815, which was filed on Nov. 18, 2005, which was a continuation of International Patent Application No. PCT/JP2004/007221, filed on May 20, 2004, and claims priority to Japanese Patent Application No. 2003-142681, filed on May 20, 2003, both of which are incorporated herein by reference in their entireties.

BACKGROUND OF THE INVENTION

1. Field of the Invention

The present invention relates to amide derivatives which have superior anti-inflammatory and analgesic activities, and pharmaceutical compositions which comprise such an amide derivative as an active ingredient. The present invention further relates to methods of using such an amide derivative and such a pharmaceutical composition.

2. Discussion of the Background

It is considered that pain is developed by direct stimuli from damage and invasion of tissue based on various exogenous factors, amplified by various endogenous algetic substances produced by tissue damage and results in inflammatory conditions (Tanaka et al. ed.: NEW Yakurigaku, Nankodo Co., Ltd., Apr. 15, 2002, pp. 354-355). In addition, there is a pain caused by a functional abnormality of the peripheral nervous system or central nervous system, rather than tissue damage, which is referred to as a neuropathic pain.

As therapeutic drugs for these pains, a wide variety of drugs have already been known, which are largely divided with respect to the aspects of action mechanism into opioid analgesics which contain narcotic analgesics such as morphine, codeine, opium alkaloids, buprenorphine, pentazocine, and the like; and antipyretic analgesics (non-narcotic analgesics) such as aspirin, indomethacin, acetaminophen, and the like. While the former provides a strong analgesic effect by acting on the opioid receptor in the central nervous system, its use is limited because it causes severe side effects and dependency. While the latter acts on peripheral tissues to bring about an anti-inflammatory and analgesic effect, the level of the action is low and various side effects may occur. Furthermore, a therapeutic drug effective for a neuropathic pain associated with diabetic neuropathy, trigeminal neuropathy, herpes zoster, and the like has not been found yet, and the development of a pharmaceutical agent effective for a broad range of pains, including these pains, has been desired.

In recent years, during the course of studies relating to the algetic mechanism, a receptor of capsaicin (pungent component of red pepper), known to be an algetic substance, was cloned and named as a vanilloid receptor (hereinafter to be referred to as "VR1") (see, Nature, vol. 389, p. 816 (1997)).

Since VR1 present in the capsaicin-sensitive sensory nerve is activated not only by a capsaicin-like substance but also by heat, acid (H+), and the like, VR1 is considered to be involved in pain and inflammation associated with various pathologies.

To be specific, when VR1 is activated by the stimuli of capsaicin and the like, the cation channel opens, the membrane is depolarized and neuropeptide is released, which in turn evokes pain and inflammation. Therefore, a substance that antagonizes the activation of VR1 is potentially a superior therapeutic drug for pain and inflammation. In fact, capsazepine, known to be a VR1 receptor antagonist, has been reported to show a remarkable analgesic effect in animal models (see, Life Science, vol. 69, p. 2911 (2001)).

On the other hand, the VR1 agonist capsaicin is also considered to develop intense stimuli (pain) and then induce an analgesic effect or anti-inflammatory effect. It is postulated that capsaicin binds to a receptor to continuously open the VR1 cation channel, which in turn makes the sensory nerve unresponsive to stimuli (see, Pharmacol. Rev., vol. 51, p. 159 (1999)). Since capsaicin has been, in fact, effectively used as an analgesic for pain in diseases such as diabetic neuropathy, rheumatoid arthritis, and the like, a compound (VR1 agonist) having a capsaicin-like action mechanism is also expected to be a therapeutic drug for pain and inflammation.

In addition, a report has been documented that patients with not only pain but also inflammatory bowel diseases (Crohn's disease, ulcerative colitis, etc.) show a high expression of VR1, and therefore, a compound having a capsaicin-like action mechanism or an action mechanism that antagonizes responses of capsaicin is expected to be a good therapeutic drug for inflammatory bowel diseases.

As diseases involving the capsaicin-sensitive sensory nerve, pruritus, allergic and nonallergic rhinitis, hyperactive bladder frequent urination, incontinence, apoplexy, irritable bowel syndrome, respiratory diseases (asthma, chronic obstructive pulmonary disease, etc.), dermatitis, gastric ulcer, duodenal ulcer, and the like are known, and an antiobesity action for capsaicin has been reported. Therefore, a compound having a capsaicin-like action mechanism or an action mechanism that antagonizes responses of capsaicin is also useful as a therapeutic drug for these diseases and conditions.

As mentioned above, a compound having a capsaicin-like action mechanism or an action mechanism that antagonizes responses to capsaicin is highly expected to be a therapeutic drug for neuropathic pain, for which existing analgesics are ineffective, such as diabetic neuropathy and the like, as well as pains caused by various diseases such as rheumatoid arthritis and the like, and further, apart from pain, a therapeutic drug for various diseases in which VR1 is involved, such as ulcerative colitis and the like.

As a capsaicin receptor ligand, a compound having the following formula (a) has been described in a literature

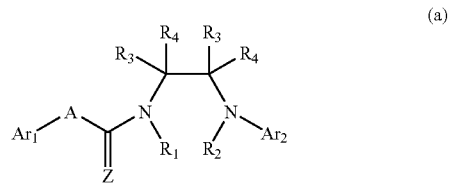

(a)

wherein A is a single bond, O, S, $NR_A$, $CR_BR_{B''}$, and the like, Z is O or S, $R_1$ and $R_2$ are each H or alkyl, $R_3$ and $R_4$ are each H, halogen, hydroxy, amino, and the like, or adjacent $R_3$ and $R_4$ are bonded to form an aryl ring and the like, and $Ar_1$ and $Ar_2$ are each optionally substituted cycloalkyl and the like (see, WO02/08221).

In addition, as a vanilloid receptor antagonist, a heterocyclic compound having a urea bond (see, WO02/072536, WO02/090326, and WO03/022809), a thiocarbamic acid derivative (see, WO02/16317), a thiourea derivative (see, WO02/16318 and WO02/16319), a trialkylglycine derivative (see, WO02/28885) and a pyridine derivative (see, WO02/076946) have been reported.

Moreover, a cyanophenyl derivative of the formula (b)

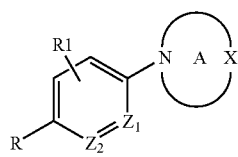

(b)

wherein ring A is an optionally substituted 4-8-membered saturated heterocycle, $Z_1$ and $Z_2$ are each CH or a nitrogen atom, X is an oxygen atom, $C(R^2)R^3$, and the like, R is cyano or a nitro group, and each $R^1$ is H, halogen, cyano, lower halogenoalkyl, and the like has been reported as an androgen antagonist (see, JP-A-2002-88073).

However, none of these compounds has the structural characteristics of the compound of the below-mentioned formula (I).

SUMMARY OF THE INVENTION

Accordingly, it is one object of the present invention to provide novel compounds which exhibit superior anti-inflammatory activity.

It is another object of the present invention to provide novel compounds which exhibit superior analgesic activity.

It is another object of the present invention to provide novel compounds which exhibit superior anti-inflammatory and analgesic activities.

It is another object of the present invention to provide novel pharmaceutical compositions which contain such a compound.

It is another object of the present invention to provide novel methods for treating inflammation with such a compound or pharmaceutical composition.

It is another object of the present invention to provide novel methods for treating pain with such a compound or pharmaceutical composition.

It is another object of the present invention to provide novel methods for treating inflammatory bowel diseases (Crohn's disease, ulcerative colitis, etc.), hyperactive bladder frequent urination, incontinence, irritable bowel syndrome, respiratory diseases (asthma, chronic obstructive pulmonary disease, etc.), diabetic neuropathy, and rheumatoid arthritis with such a compound or pharmaceutical composition.

These and other objects, which will become apparent during the following detailed description, have been achieved by the inventors' discovery that amide derivatives, which have a particular chemical structure, have superior anti-inflammatory and analgesic activities and are useful as pharmaceutical agents.

Accordingly, the present invention provides amide compounds represented by the following formula (I), and pharmaceutical compositions which comprise such an amide compound as an active ingredient, particularly, pharmaceutical compositions useful as therapeutic agent for inflammatory bowel diseases (Crohn's disease, ulcerative colitis, etc.), hyperactive bladder frequent urination, incontinence, irritable bowel syndrome, respiratory diseases (asthma, chronic obstructive pulmonary disease etc.), diabetic neuropathy, rheumatoid arthritis and the like, as a pharmaceutical agent having an anti-inflammatory and analgesic action.

Thus, the present invention provides amide compounds represented by the formula (I):

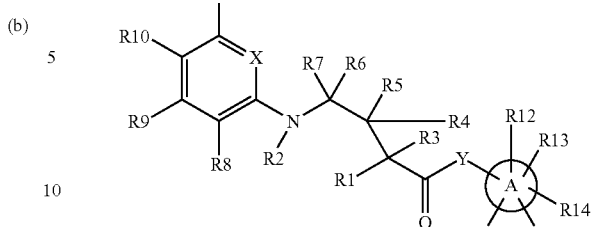

(I)

wherein:
A is a cycloalkyl group, an aryl group, or a heteroaryl group;
X is a nitrogen atom or CR17;
Y is —NRa-, —(CRbRb')m-, —NRa-(CRbRb')m-, —NRa-(CRbRb')m-O—, or —NRa'-(CRbRb')m-NRa-;
m is an integer of 0 to 4;
Ra, Ra', Rb, Rb', R1, R2, R3, R4, R5, R6, R7, R8, R9, R10, R11, R12, R13, R14, R15, R16, and R17 may be the same or different, and each is a hydrogen atom, a halogen atom, a cyano group, a nitro group, an ammonium group, an alkyl group optionally having one or more substituents, an alkenyl group optionally having one or more substituents, an alkynyl group optionally having one or more substituents, a cycloalkyl group optionally having one or more substituents (optionally having one or more hetero atoms in the ring), a cycloalkylalkyl group optionally having one or more substituents (optionally having one or more hetero atoms in the ring), an aryl group optionally having one or more substituents, an aralkyl group optionally having one or more substituents, a heteroaryl group optionally having one or more substituents, a heteroarylalkyl group optionally having one or more substituents, or
-ZR18, wherein:
Z is —O—, —S(O)p-, —S(O)pO—, —NH—, —NR19-, —C(=O)—, —C(=O)O—, —C(=O)NH—, —C(=O)NR19-, —S(O)pNH—, —S(O)pNR19-, —NHC(=O)—, —NR19C(=O)—, —NHS(O)p-, or —NR19S(O)p-, wherein:
p is an integer of 0 to 2, and
R18 and R19 may be the same or different and each is a hydrogen atom, an alkyl group optionally having one or more substituents, an alkenyl group optionally having one or more substituents, an alkynyl group optionally having one or more substituents, a cycloalkyl group optionally having one or more substituents (optionally having one or more hetero atoms in the ring), a cycloalkylalkyl group optionally having one or more substituents (optionally having one or more hetero atoms in the ring), an aryl group optionally having one or more substituents, an aralkyl group optionally having one or more substituents, a heteroaryl group optionally having one or more substituents, a heteroarylalkyl group optionally having one or more substituents, or an acyl group, or R18 and R19 may be bonded to form a ring, or
R3 and R4 are optionally bonded to form a carbon-carbon bond, or of R8, R9, R10, R11, R12, R13, R14, R15 and R16, those bonded to the adjacent carbon atom are optionally bonded to each other to form, together with the carbon atom constituting ring A, a saturated or unsaturated ring optionally having one or more hetero atoms in the ring formed, or
when Y is —NRa-, Ra is optionally bonded to one of R12, R13, R14, R15, and R16 to form a ring together with the carbon atom constituting ring A, ring, or R1 and R2 in combination optionally form a ring, as shown in the following formula (II)

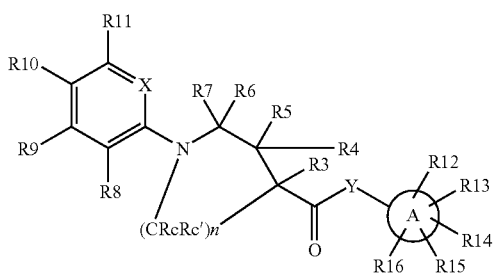

wherein:
n is an integer of 1 to 3,
Rc and Rc' are as defined for Ra, and
R10 is the above-mentioned substituents except a nitro group, a cyano group, and a trifluoromethyl group,
and pharmaceutically acceptable salts thereof, and hydrates thereof, and solvates thereof.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
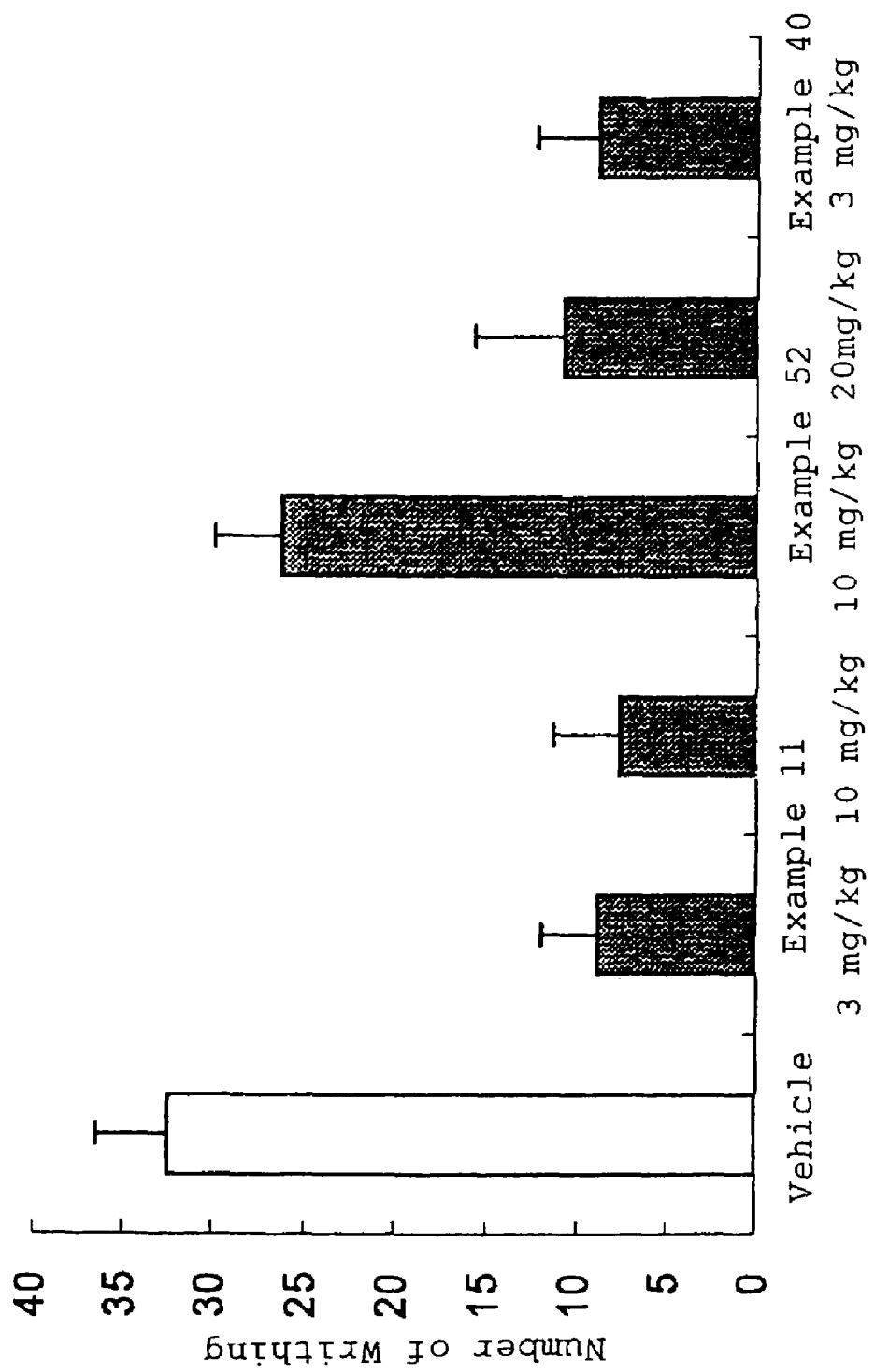
FIG. 1 is a graph showing the number of writhing for the compound of the present invention by the acetic acid-induced writhing method.

The present invention will now be described in more detail.

As the "cycloalkyl group" for A in the formula (I), a saturated or unsaturated cycloalkyl group having 3 to 8 carbon atoms such as cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, and the like can be mentioned, as the "aryl group" for A, a monocyclic or polycyclic aryl group such as phenyl, naphthyl, tetrahydronaphthyl, indanyl, anthranyl, phenanthryl, and the like can be mentioned, as the "heteroaryl group" for A, a 5-membered or 6-membered aromatic heterocyclic group optionally condensed with a benzene ring or with the same or different heterocycle such as imidazolyl, pyrazolyl, furyl, thienyl, pyridyl, pyrimidinyl, pyrazinyl, indazolyl, oxazolyl, thiazolyl, oxadiazolyl, benzopyrazolyl, benzimidazolyl, benzoxazolyl, benzothiazolyl, quinolyl, isoquinolyl, and phthalazinyl, and the like can be mentioned.

As the "halogen atom" for Ra, Ra', Rb, Rb', Rc, Rc', R1, R2, R3, R4, R5, R6, R7, R8, R9, R10, R11, R12, R13, R14, R15, R16 or R17, fluorine, chlorine, bromine, and iodine can be mentioned.

As the alkyl group of the "alkyl group optionally having one or more substituents" for Ra, Ra', Rb, Rb', Rc, Rc', R1, R2, R3, R4, R5, R6, R7, R8, R9, R10, R11, R12, R13, R14, R15, R16, R17, R18 or R19, a straight chain and branched alkyl group having 1 to 9 carbon atoms such as methyl, ethyl, propyl, isopropyl, butyl, isobutyl, t-butyl, n-pentyl, isopentyl, n-hexyl, isohexyl, n-octyl, isooctyl, n-nonyl, and the like can be mentioned. As the alkenyl group of the "alkenyl group optionally having one or more substituents," an alkenyl group having 2 to 9 carbon atoms, which contains each isomer of vinyl, allyl, propenyl, butenyl, pentenyl, hexenyl, heptenyl, and the like, can be mentioned.

As the alkynyl group of the "alkynyl group optionally having one or more substituents," an alkynyl group having 2 to 9 carbon atoms, which contains each isomer of ethynyl, propynyl, butynyl, pentynyl, and the like, can be mentioned.

As the cycloalkyl group of the "cycloalkyl group optionally having one or more substituents," and "cycloalkylalkyl group optionally having one or more substituents," a saturated or unsaturated cycloalkyl group having 3 to 8 carbon atoms such as cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, and the like can be mentioned. The carbon atom of the cycloalkyl ring is optionally replaced by one or two, the same or different hetero atoms selected from nitrogen, oxygen, and sulfur.

As the alkyl moiety of the "cycloalkylalkyl group optionally having one or more substituents," an alkylene having 1 to 6 carbon atoms such as methylene, ethylene, and propylene, and the like can be mentioned.

As the aryl group of the "aryl group optionally having one or more substituents," a monocyclic or polycyclic aryl group such as phenyl, naphthyl, tetrahydronaphthyl, indanyl, anthranyl, phenanthryl, and the like can be mentioned.

As the aralkyl group of the "aralkyl group optionally having one or more substituents," an aralkyl group, which has an alkylene group having 1 to 5 carbon atoms in the aforementioned aryl ring, such as benzyl, phenethyl, and naphthylmethyl, and the like, can be mentioned.

As the heteroaryl group of the "heteroaryl group optionally having one or more substituents," and "heteroarylalkyl group optionally having one or more substituents," a 5-membered or 6-membered aromatic heterocycle optionally condensed with a benzene ring or the same or different heterocycle, such as imidazolyl, pyrazolyl, furyl, thienyl, pyridyl, pyrimidinyl, pyrazinyl, indazolyl, oxazolyl, thiazolyl, oxadiazolyl, benzopyrazolyl, benzimidazolyl, benzoxazolyl, benzothiazolyl, quinolyl, isoquinolyl, phthalazinyl, and the like, can be mentioned. When it is condensed with a benzene ring, the binding site with Y may be on any of the heteroaryl ring and the benzene ring.

As the alkyl moiety of the "heteroarylalkyl group optionally having one or more substituents," an alkylene having 1 to 6 carbon atoms, such as methylene, ethylene, propylene and the like, can be mentioned.

As the substituent for these " . . . optionally having one or more substituents," for example, alkyl group, alkenyl group, alkynyl group, cycloalkyl group (optionally having one or more hetero atoms in the ring), aryl group, heteroaryl group, alkoxy group, alkylthio group, cycloalkyloxy group (optionally having one or more hetero atoms in the ring), cycloalkylthio group (optionally having one or more hetero atoms in the ring), aryloxy group, aralkyloxy group, arylthio group, heteroaryloxy group, heteroarylalkyloxy group, heteroarylthio group, halogenoalkyl group, halogenoalkoxy group, nitro group, amino group, mono- or di-alkylamino group, alkyloxycarbonyl group, alkanoyl group, aroyl group, alkylsulfonyl group, sulfamoyl group, carbamoyl group, mono- or di-alkylcarbamoyl group, sulfamoyl group, mono- or di-alkylsulfamoyl group, alkylsulfonylamino group, arylsulfonylamino group, hydroxyl group, halogen atom, cyano group, oxo group, carboxyl group, and the like can be mentioned.

As the "acyl group" for R18 or R19, a saturated or unsaturated, aliphatic or aromatic acyl group, such as formyl, acetyl, propionyl, butyryl, valeryl, pivaloyl, succinyl, acryloyl, crotonoyl, benzoyl, naphthoyl, toluoyl, and the like, can be mentioned.

As the ring formed by R18 and R19 bonded to each other, a 5- to 7-membered ring optionally further having, besides nitrogen atom, 1-3 hetero atoms selected from nitrogen, oxygen, and sulfur can be mentioned.

As the saturated or unsaturated ring formed by those bonded to the adjacent carbon atom, out of R8, R9, R10, R11, R12, R13, R14, R15 and R16, together with the carbon atom constituting ring A, a 5- to 7-membered ring optionally having, as a ring-constituting atom, 1-3 hetero atoms selected from nitrogen, oxygen, and sulfur can be mentioned.

When Y is —NRa-, as the ring formed by Ra bonded with one of R12, R13, R14, R15 and R16, together with the carbon atom constituting ring A, a 5 to 7-membered ring optionally further having, as a ring-constituting atom besides nitrogen atom, 1 to 3 hetero atoms selected from nitrogen, oxygen, and sulfur can be mentioned.

In formula (I) and formula (II), a compound wherein A is a cycloalkyl group, a phenyl group, an isoquinolyl group, a pyridyl group, an indazolyl group, or a benzothiazolyl group is preferable.

In formula (II), a compound wherein R3 and R4 are bonded to form a carbon-carbon bond is preferable.

In formula (II), a particularly preferable compound is a compound wherein:
A is a phenyl group, an isoquinolyl group, a pyridyl group, an indazolyl group, a benzothiazolyl group, or a cycloalkyl group;
X is a nitrogen atom, or CH;
Y is —NH—, or —NH—CH$_2$—;
n is 2;
Rc, Rc', R3, R4, R5, R6, R7, R9, R10, and R11 are each a hydrogen atom;
R8 is a trifluoromethyl group, a chlorine atom, a nitro group, or a cyano group;
R12, R13, R14, R15 and R16 may be the same or different, each is a hydrogen atom, a fluorine atom, a chlorine atom, a bromine atom, an iodine atom, a methyl group, an ethyl group, a vinyl group, an isopropyl group, a trifluoromethyl group, a t-butyl group, an n-pentyl group, an n-octyl group, a methoxy group, an amino group, a cyano group, a nitro group, a hydroxyl group, a thiol group, a methoxycarbonyl group, a hydroxymethyl group, a methanesulfonylamino group, an aminoethoxy group, or a benzoyl group; and
R3 and R4 are bonded to form a carbon-carbon bond, and an embodiment wherein A is a phenyl group, an isoquinolyl group, a pyridyl group, an indazolyl group, or a benzothiazolyl group is more preferable.

Of the amide derivatives represented by the above-mentioned formula (I), the compounds represented by the following formula (III) and (IV) are preferable since they are superior in analgesic and antiinflammatory activities.

An amide derivative represented by the formula (III):

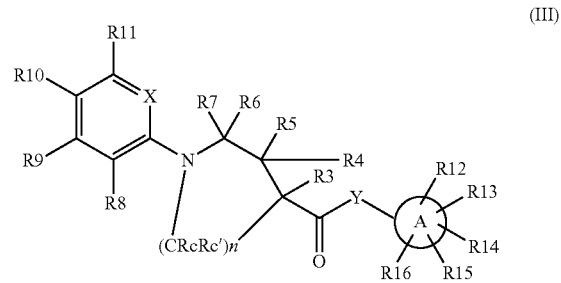

(III)

wherein:
A is any of an aryl group, a heteroaryl group, and a cycloalkyl group;
X is a nitrogen atom or CR17;
Y is —NRa-, or —NRa-(CRbRb')m-;
n is 2;
m is 1;
Ra, Rb, Rb', Rc and Rc' are each a hydrogen atom;
R3, R4, R5, R6, and R7 are each a hydrogen atom;
R8 is an alkyl group optionally having one or more substituents, a halogen atom, a nitro group, or a cyano group;
R9, R10 and R11 are each a hydrogen atom; and
R12, R13, R14, R15, R16, and R17 may be the same or different and each is a hydrogen atom, a halogen atom, a cyano group, a nitro group, an alkyl group optionally having one or more substituents, an alkenyl group optionally having one or more substituents, or -ZR18, wherein
Z is —NR19-, —NHC(=O)—, —O—, —C(=O)—, —NH—, —NHS(O)$_2$—, —C(=O)O—, or —S—; and
R18 and R19 may be the same or different, and each is a hydrogen atom, an alkyl group optionally having one or more substituents, or an aryl group optionally having one or more substituents, or
R3 and R4 are optionally bonded to form a carbon-carbon bond, a pharmaceutically acceptable salt thereof, a hydrate thereof, or a solvate thereof.

In formula (III), the "aryl group", "heteroaryl group" and "cycloalkyl group" for A, the "alkyl group optionally having one or more substituents" for R8, R12, R13, R14, R15, R16, R17, R18 or R19, the "alkenyl group optionally having one or more substituents" for R12, R13, R14, R15, R16 or R17, and the "aryl group optionally having one or more substituents" for R18 or R19 are as exemplified for the formula (I).

In the formula (III), a compound wherein A is an aryl group or a heteroaryl group is preferable.

In the formula (III), a compound wherein R3 and R4 are bonded to form a carbon-carbon bond is preferable.

In the formula (III), a particularly preferable compound is a compound wherein:
A is a phenyl group, an isoquinolyl group, a pyridyl group, an indazolyl group, or a benzothiazolyl group;
X is a nitrogen atom or CH;
Y is —NH—, or —NH—CH$_2$—;
n is 2,
Rc, Rc', R3, R4, R5, R6, R7, R9, R10, and R11 are each a hydrogen atom;
R8 is a trifluoromethyl group, a chlorine atom, a nitro group, or a cyano group; and
R12, R13, R14, R15, and R16 may be the same or different and each is a hydrogen atom, a fluorine atom, a chlorine atom, a bromine atom, an iodine atom, a methyl group, an ethyl group, a vinyl group, an isopropyl group, a trifluoromethyl group, a t-butyl group, an n-pentyl group, an n-octyl group, a methoxy group, an amino group, a cyano group, a nitro group, a hydroxyl group, a thiol group, a methoxycarbonyl group, a hydroxymethyl group, a methanesulfonylamino group, an aminoethoxy group, or a benzoyl group, or R3 and R4 are optionally bonded to form a carbon-carbon bond.

An amide derivative represented by the formula (IV):

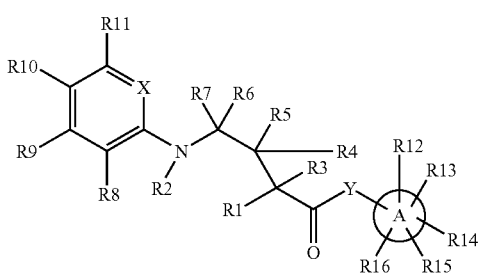

(IV)

wherein:

A is an aryl group or a heteroaryl group;

X is CR17;

Y is —NRa-;

Ra is a hydrogen atom, or an alkyl group optionally having one or more substituents;

R2 is an alkyl group optionally having one or more substituents;

R1, R3, R4, R5, R6, R7, R8, R10, R11, and R17 are each a hydrogen atom,

R9 is an alkyl group optionally having one or more substituents; and

R12, R13, R14, R15, and R16 may be the same or different and each is a hydrogen atom, a halogen atom, an alkyl group optionally having one or more substituents, or -ZR18, wherein Z is —O—; and R18 is an alkyl group optionally having one or more substituents; or of R12, R13, R14, R15, and R16, those bonded to the adjacent carbon are optionally bonded to each other to form, together with the carbon atom constituting ring A, a saturated or unsaturated ring optionally having one or more hetero atoms in the ring formed; or one of R12, R13, R14, R15, and R16 is optionally bonded to Ra to form a ring together with the carbon atom constituting ring A, a pharmaceutically acceptable salt thereof, a hydrate thereof, or a solvate thereof.

The "aryl group" and "heteroaryl group" for A in formula (IV), the "alkyl group optionally having one or more substituents" for Ra, R2, R9, R12, R13, R14, R15, R16 or R18, the saturated or unsaturated ring formed by those of R12, R13, R14, R15 and R16, which are bonded to the adjacent carbon atom, together with the carbon atom constituting ring A, and the ring formed by one of R12, R13, R14, R15, and R16 bonded to Ra together with the carbon atom constituting ring A are as exemplified for the formula (I).

In the formula (IV), a particularly preferable compound is a compound wherein:

A is a phenyl group, a quinolyl group, or a naphthyl group;

X is CH;

Y is —NH—; or the formula (V):

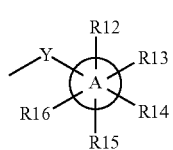

(V)

is the formula (VI)

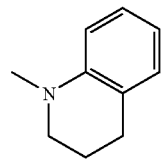

(VI)

R2 is an ethyl group;

R1, R3, R4, R5, R6, R7, R8, R10, R11, and R17 are each a hydrogen atom;

R9 is a methyl group; and

R12, R13, R14, R15, and R16 may be the same or different and each is a hydrogen atom, a fluorine atom, a bromine atom, a trifluoromethoxy group, a methoxy group, or a t-butyl group; or of R12, R13, R14, R15, and R16, those bonded to the adjacent carbon atom are optionally bonded to each other to form, together with the carbon atom constituting ring A, a saturated or unsaturated ring optionally having one or more hetero atoms in the ring formed.

In the present invention, specific examples of the particularly preferable compound include the compounds shown below:

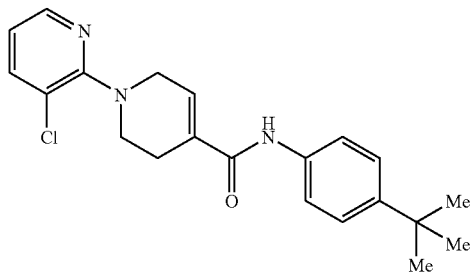

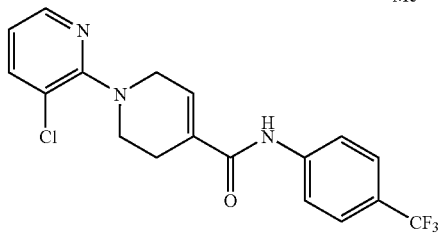

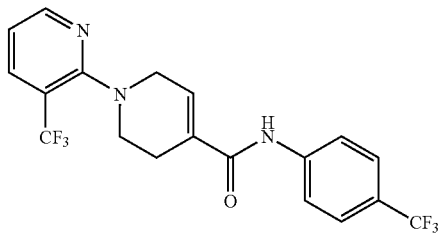

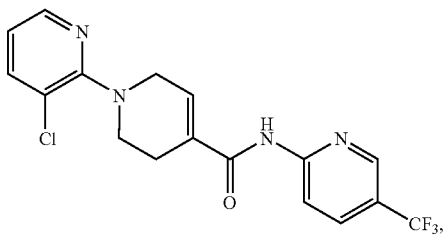

pharmaceutically acceptable salts thereof, hydrates thereof, and solvates thereof.

As the pharmaceutically acceptable salts in the present invention, salts with inorganic acid such as hydrochloric acid, hydrobromic acid, sulfuric acid, nitric acid, phosphoric acid, and the like; salts with inorganic base such as sodium, potassium, magnesium, calcium, aluminum, lithium and the like; salts with organic acid such as formic acid, oxalic acid, maleic acid, tartaric acid, citric acid, benzoic acid, benzenesulfonic acid, toluenesulfonic acid, trifluoroacetic acid, and the like; salts with organic base such as trimethylamine, triethylamine, diethanolamine, triethanolamine, dibenzylethylenediamine, dicyclohexylamine, procaine, and the like; salts with amino acid such as arginine, aspartic acid, glutamic acid, lysine, ornithine, and the like; and the like can be mentioned.

The compounds of formulas (I)-(IV) encompass optical isomers, geometric isomers, and mixtures thereof at optional ratios.

The compounds of formulas (I)-(IV) can be produced by, for example, the following reaction schemes.

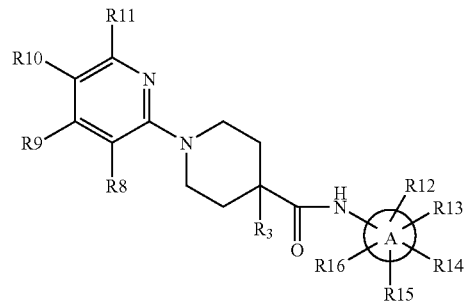

X' = F, Cl, Br, I
R = Me, Et wherein each symbol is as defined above.

For example, the corresponding pyridine compound (1) is subjected to reaction with isonipecotic acid derivative like (2) using, for example, dimethylformamide and the like as a solvent and, for example, potassium carbonate and the like as a base, and then hydrolysis using, for example, ethanol and the like as a solvent and, for example, aqueous sodium hydroxide solution and the like as a base to give (3). Thereafter (3) is converted to acid halide using, for example, thionyl chloride and the like, and the acid halide is condensed with various amine derivatives such as (4) using, for example, dichloromethane and the like as a solvent and, for example, triethylamine and the like as a base to give amide derivative (Ia).

The derivative (Ib) of the formula (I) wherein X is CR17, Y is NH, and R2 is an alkyl group can be synthesized according to the following reaction scheme.

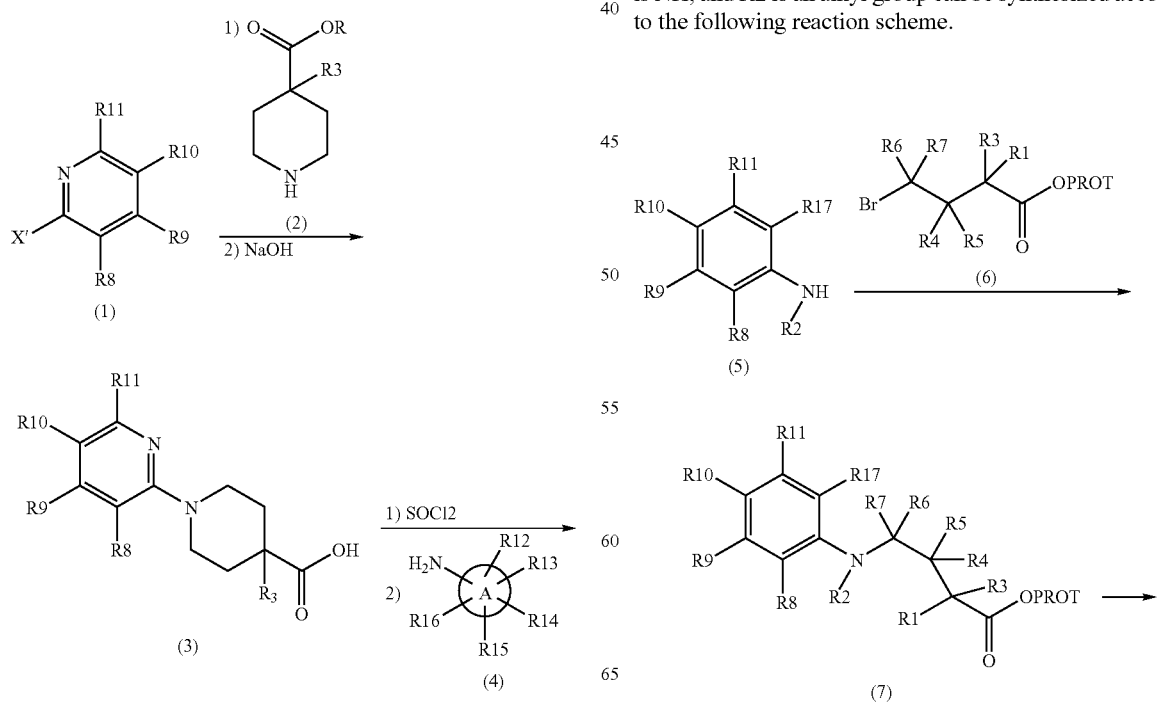

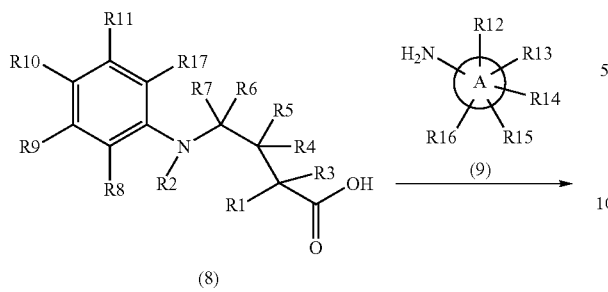

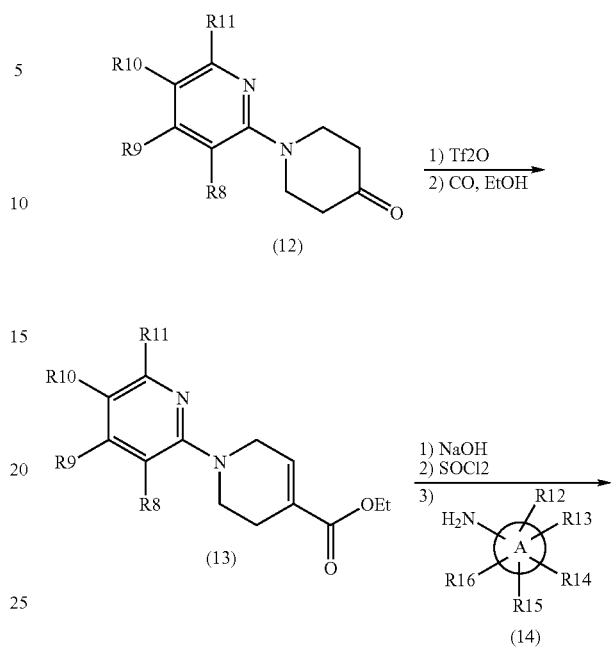

wherein PROT is a lower alkyl group, and other symbols are as defined above.

N-Alkylaniline (5) having a desired substituent is reacted with bromide represented by (6), whose PROT is lower alkyl, in a solvent such as DMF and the like, in the presence of a base such as potassium carbonate and the like, to give dialkylaniline (7). The obtained (7) is subjected to hydrolysis under appropriate conditions, such as treatment with an aqueous lithium hydroxide solution in, for example, a solvent such as THF (tetrahydrofuran) and the like, or treatment with a solution of hydrogen chloride in 1,4-dioxane and the like, under aqueous conditions, and the like to give carboxylic acid (8). Condensation of the obtained (8) with amine (9) in a solvent such as DMF, dichloromethane and the like in the presence of a condensing agent such as DIC (diisopropylcarbodiimide) and the like, together with a suitable additive as necessary, such as HOAt (1-hydroxy-7-aza-benzotriazole), HOBt (1-hydroxybenzotriazole) and the like, and the like gives (Ib).

The derivative (Ic) of the formula (I), wherein X is a nitrogen atom, Y is NH, R1 and R2 in combination form a ring, and R3 and R4 form a carbon-carbon bond, can be synthesized according to the following reaction scheme.

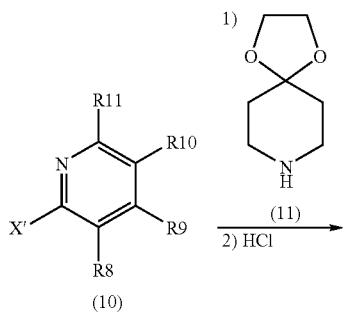

X' = F, Cl, Br, I

The corresponding pyridine compound (10) is subjected to reaction with, for example, a piperidine derivative like (11) using, for example, dimethylformamide and the like as a solvent, for example, potassium carbonate and the like as a base and then hydrolysis using, for example, ethanol and the like as a solvent and, for example, hydrochloric acid and the like as acid to give (12). (12) is subjected to reaction with trifluoromethanesulfonic anhydride and the like using, for example, tetrahydrofuran and the like as a solvent in the presence of a suitable base such as lithium diisopropylamide etc. and then reaction with carbon monoxide and, for example, alcohol such as ethanol etc. using, for example, dimethylformamide and the like as a solvent in the co-presence of, for example, a catalyst such as palladium acetate etc. and, for example, triethylamine etc. as a base to give (13). (13) is subjected to hydrolysis using, for example, aqueous sodium hydroxide solution etc. as a base, and then conversion to acid halide using thionyl chloride and the like, and the acid halide is condensed with various amine derivatives such as (13) using, for example, dichloromethane and the like as a solvent and, for example, triethylamine and the like as a base to give amide derivative (Ic).

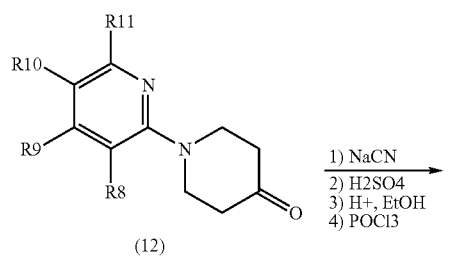

(12)

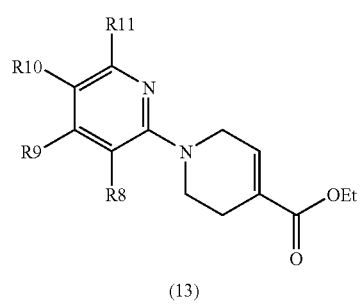

(13)

Alternatively, (12) is subjected to reaction with sodium cyanide and the like using, for example, diethyl ether, water and the like as a solvent, in the presence of a suitable base such as sodium hydrogen carbonate etc., and then hydrolysis using, for example, sulfuric acid and the like as a solvent, and then esterification using, for example, ethanol and the like as a solvent, in the presence of, for example, sulfuric acid etc. as an acid and then dehydration reaction using, for example, phosphorus oxychloride and, for example, pyridine and the like as a solvent to give (13). (13) is subjected to the aforementioned reactions to give amide derivative (Ic).

A general synthetic method of the ring A moiety is as follows:

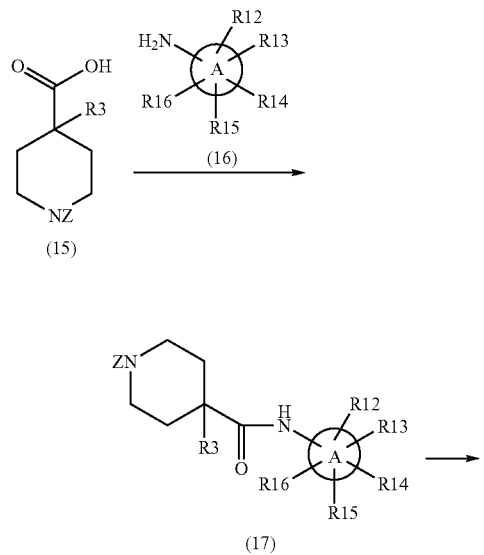

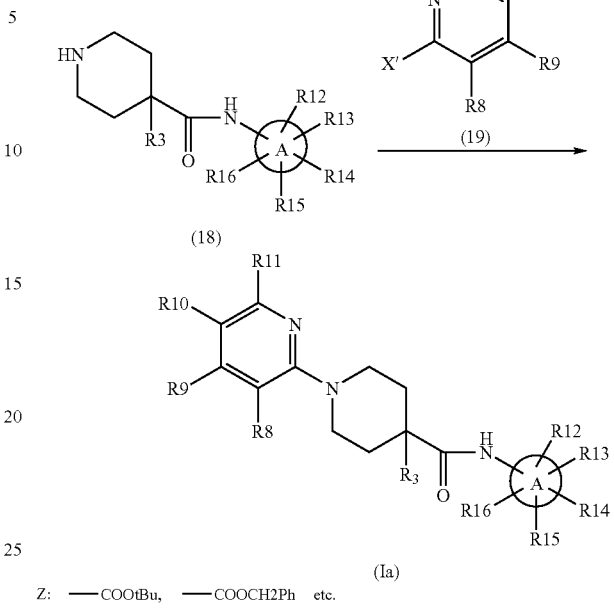

Z: —COOtBu, —COOCH2Ph etc.
X' = F, Cl, Br, I

The corresponding isonipecotic acid derivative (15) is condensed with various amine derivatives such as (16) in the presence of a condensing agent such as DIC (diisopropylcarbodiimide) etc. together with a suitable additive such as HOAt (1-hydroxy-7-aza-benzotriazole), HOBt (1-hydroxy-benzotriazole) etc. as necessary using, for example, dichloromethane and the like as a solvent and triethylamine and the like as a base to give (17). (17) is processed using, for example, dioxane and the like as a solvent and, for example, hydrochloric acid and the like as acid to give (18). (18) is reacted with, for example, a pyridine derivative such as (19) using, for example, ethanol and the like as a solvent, and, for example, triethylamine and the like as a base to give amide derivative (Ia).

Various compounds of the present invention and intermediates obtained by the aforementioned production method can be converted to various compounds of the present invention and intermediates having an amino group having a substituent by further subjecting the compounds to each reaction such as alkylation, acylation, halogenation, nucleophilic substitution, and the like. The alkylation and nucleophilic substitution reaction can be performed by, for example, methods described in The Chemical Society of Japan ed. "Jikkenkagaku Koza, 4th edition" vol. 20 (1992) (Maruzen Co., Ltd.) etc., acylation can be performed by, for example, the method described in The Chemical Society of Japan ed. "Jikkenkagaku Koza, 4th edition" vol. 22 (1992) (Maruzen Co., Ltd.) etc., and halogenation can be performed by, for example, The Chemical Society of Japan ed. "Jikkenkagaku Koza, 4th edition" vol. 19 (1992) (Maruzen Co., Ltd.) etc.

Since the amide derivative of the formula (I) has a superior anti-inflammatory and analgesic activity, and is a capsaicin-like active substance or antagonizes the action of capsaicin, it is suitable as a therapeutic agent for general pain treatment of headache, toothache, muscle pain, menstrual pain, wound pain and the like, neuropathic pain associated with diabetic neuropathy, trigeminal neuropathy, herpes zoster, hyperalgesia and the like, or inflammatory bowel disease (Crohn's disease, ulcerative colitis, etc.), rheumatoid arthritis, osteoarthritis, Raynaud's disease, pruritus, allergic and nonallergic rhinitis, cystitis, frequent urination, incontinence, apoplexy, irritable bowel syndrome, respiratory diseases (asthma, chronic obstructive pulmonary disease, etc.), dermatitis, gastric ulcer, duodenal ulcer and the like, and particularly useful as a therapeutic agent for inflammatory bowel disease, frequent urination, incontinence and asthma.

While the dose of the compound of the present invention varies depending on the kind of disease, pathology, age, and administration mode, it is generally 0.001 to 1000 mg, preferably 0.01 to 500 mg, more preferably 0.1 to 200 mg, per day for an adult, which is administered once or in several portions.

The administration mode of the therapeutic agent of the present invention may be any of oral administration by solid preparation or liquid and parenteral administration by preparations such as subcutaneous, intramuscular or intravenous injection, adhesive agent, suppository, inhalant, and the like. As the solid preparation, powders, granules, tablets, pills, capsules, and the like and troche for internal application can be mentioned, and as the liquid, solutions, syrups, emulsions, suspensions, and the like can be mentioned, all of which can be produced by methods known per se.

The therapeutic agent of the present invention is formulated into preparations by adding one or more appropriate pharmaceutically acceptable vehicle, carrier, such as excipient, binder, lubricant, disintegrant, coating, solvent, dissolution aids, suspending agent, emulsifier, isotonicity agent, and the like, as necessary for formulation of preparations. Where necessary, additives such as preservatives, antioxidants, coloring agents, sweetening agents, flavors, and the like can be added. The amount of the active ingredient in the composition or preparation is appropriately determined so that a suitable dose in the prescribed range can be achieved.

As the excipient, lactose, mannitol, glucose, hydroxypropylcellulose, micro crystalline cellulose, starch, polyvinylpyrrolidone, magnesium aluminometasilicate, and the like can be mentioned; as the binder, pregelatinized starch, sucrose, gelatin, gum arabic, methylcellulose, carboxymethylcellulose, carboxymethylcellulose sodium, crystalline cellulose, sucrose, D-mannitol, trehalose, dextrin, hydroxypropylcellulose, hydroxypropylmethylcellulose, polyvinylpyrrolidone, polyvinyl alcohol, and the like can be mentioned; as the lubricant, stearic acid, magnesium stearate, calcium stearate, talc, colloidal silica, and the like can be mentioned; as the disintegrant, carboxymethylcellulose calcium, lactose, sucrose, starch, carboxymethylcellulose, croscarmellose sodium, sodium carboxymethyl starch, crystalline cellulose, and the like can be mentioned, and as the coating, sucrose, gelatin, hydroxypropylcellulose, hydroxypropylmethylcellulose phthalate, and the like can be mentioned.

As the solvent, hydrophilic solvents such as purified water, physiological brine, Ringer's solution, ethanol, propylene glycol, glycerol, polyethylene glycol, macrogol, and the like; and oily solvents such as olive oil, peanut oil, sesame oil, camellia oil, rape seed oil, fatty acid monoglyceride, fatty acid diglyceride, higher fatty acid ester, liquid paraffin, and the like can be mentioned; as the dissolution aids, polyethylene glycol, propylene glycol, D-mannitol, trehalose, benzyl benzoate, ethanol, sodium carbonate, sodium citrate, sodium salicylate, glutamic acid, aspartic acid, and the like can be mentioned; as the suspending agent, sodium lauryl sulfate, lecithin, glyceryl monostearate, polyvinyl alcohol, polyvinyl pyrrolidone, carboxymethylcellulose sodium, methylcellulose, hydroxymethylcellulose, hydroxyethylcellulose, hydroxypropylcellulose, polysorbates, polyoxyethylene hydrogenated castor oil, gum arabic, bentonite, and the like can be mentioned; as the emulsifier, gum arabic, gelatin, lecithin, egg yolk, cetanol, glyceryl monostearate, methylcellulose, carboxymethylcellulose sodium, stearic acid, and the like can be mentioned; and as the isotonicity agent, sodium chloride, potassium chloride, glucose, fructose, mannitol, sorbitol, lactose, saccharose, glycerol, urea, and the like can be mentioned.

As the preservative, paraoxybenzoates, chlorobutanol, benzyl alcohol, phenethyl alcohol, dehydroacetic acid, sorbic acid, and the like can be mentioned; and as the antioxidant, sulfite, ascorbic acid, and the like can be mentioned.

Any other pharmaceutical additive can be used for the production of the therapeutic agent of the present invention, and a sustained-release preparation can be prepared on demand.

The pharmaceutical preparation of the present invention can be formed into a package which also contains a written matter explaining use of the pharmaceutical preparation.

The amide derivatives of the present invention can be used concurrently with other analgesic, anti-inflammatory agent or therapeutic drug for each disease mentioned above. In this case, a concomitant drug may be contained in the same preparation with the amide derivative, or may be administered, as a separate preparation, simultaneously or with an appropriate time difference in association with each other.

Other features of the invention will become apparent in the course of the following descriptions of exemplary embodiments which are given for illustration of the invention and are not intended to be limiting thereof.

EXAMPLES

In the following examples, the structures of the compounds produced in the respective Examples are shown in Tables 1-15.

Example 1

Synthesis of 3'-trifluoromethyl-3,4,5,6-tetrahydro-2H-[1,2']-bipyridinyl-4-carboxylic acid (4-isopropylphenyl)amide Step 1: 3'-trifluoromethyl-3,4,5,6-tetrahydro-2H-[1,2']-bipyridinyl-4-carboxylic acid ethyl ester Dimethylformamide (100 ml) was added to 2-chloro-3-trifluoromethylpyridine (2 g, 11 mmol), ethyl isonipecotate (2 g, 12.7 mmol), and potassium carbonate (2.6 g, 18.8 mmol), and the mixture was stirred overnight at 100° C. Using ethyl acetate as an extraction solvent, the mixture was treated by a conventional method to give a crude product, which was then purified by silica gel column chromatography to give an ester intermediate (1.17 g, 3.9 mmol).

Step 2: 3'-trifluoromethyl-3,4,5,6-tetrahydro-2H-[1,2']-bipyridinyl-4-carboxylic acid The ester intermediate (1.17 g, 3.9 mmol) obtained in Step 1 was dissolved in concentrated hydrochloric acid (10 ml) and dioxane (10 ml). The mixture was stirred at 60° C. for 4 hours, and the solvent was evaporated to give a carboxylic acid intermediate.

Step 3: 3'-trifluoromethyl-3,4,5,6-tetrahydro-2H-[1,2']-bipyridinyl-4-carboxylic acid (4-isopropylphenyl) amide 1-Ethyl-3-(3-dimethylaminopropyl)carbodiimide hydrochloride (15 mg), dichloromethane (2 ml), 4-isopropylaniline (11 mg), and triethylamine (20 µl) were added to the compound (20 mg) obtained in Step 2, and the mixture was stirred at room temperature for 17 hours. The solvent was evaporated and the obtained crude product was purified by reversed phase high performance liquid chromatography (reversed phase HPLC) (water-acetonitrile, each containing 0.1% trifluoroacetic acid (TFA)) to give the title compound.

Examples 2-51

The compounds of Examples 2-51 shown in Tables 1-6 were synthesized in the same manner as in the Steps of Example 1 and using the corresponding amine instead of 4-isopropylaniline of Example 1, Step 3. It is possible to synthesize a pyridinepiperidinecarboxylic acid derivative by variously modifying the pyridine derivative and piperidine derivative in Step 1, Example 1. The final compound was purified by silica gel chromatography (hexane-ethyl acetate) or reversed phase high performance liquid chromatography (reversed phase HPLC) (water-acetonitrile, each containing 0.1% trifluoroacetic acid (TFA)).

TABLE 1

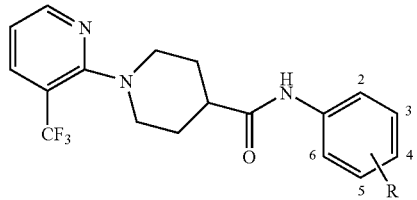

| Ex | R | [M + H]+ | NMR |
|---|---|---|---|
| 1 | 4-iPr | 392 | d1 H-NMR (300 MHz, DMSO-d6) δ 1.14 (3 H, s), 1.16 (3 H, s), 1.67-1.81 (4 H, m), 2.46-2.56 (3 H, m), 2.75-2.98 (3 H, m), 3.47-3.59 (2 H, m), 7.13 (2 H, d), 7.18 (1 H, d), 7.49 (2 H, d), 8.03 (1 H, d), 8.51 (1 H, d), 9.83 (1 H, s). |
| 2 | 4-CF3 | 418 | d 1H-NMR (300 MHz, DMSO-d6) δ 1.63-1.98 (4 H, m), 2.51-2.63 (3 H, m), 2.83-2.99 (2 H, m), 3.47-3.60 (2 H, m), 7.16 (1 H, dd), 7.64 (2 H, d), 7.81 (2 H, d), 8.04 (1 H, d), 8.51 (1 H, d). |
| 3 | 4-tBu | 406 | d1 H-NMR (300 MHz, DMSO-d6) δ 1.23 (9 H, s), 1.63-1.95 (4 H, m), 2.51-2.58 (1 H, m), 2.83-2.97 (2 H, m), 3.47-3.60 (2 H, m), 7.15 (1 H, dd), 7.27 (2 H, d), 7.50 (2 H, d), 8.03 (1 H, d), 8.51 (1 H, d). |
| 4 | 4-Me | 364 | d1 H-NMR (300 MHz, DMSO-d6) δ 1.66-1.94 (4 H, m), 2.24 (3 H, s), 2.50-2.60 (1H, m), 2.84-2.98 (2 H, m), 3.52-3.60 (2 H, m), 7.09 (2 H, d), 7.21 (1 H, dd), 7.50 (2 H, d), 8.05 (1 H, d), 8.51 (1 H, d). |
| 5 | 4-Et | 378 | d1 H-NMR (300 MHz, DMSO-d6) δ 1.15 (3 H, t), 1.71-1.95 (4 H, m), 2.48-2.61 (3 H, m), 2.84-2.99 (2 H, m), 3.52-3.60 (2 H, m), 7.10 (2 H, d), 7.21 (1 H, dd), 7.51 (2 H, d), 8.05 (1 H, d), 8.52 (1 H, d). |
| 6 | 3-OMe | 378 | d1 H-NMR (300 MHz, DMSO-d6) δ 1.68-1.93 (4 H, m), 2.65-2.81 (1 H, m), 2.82-2.99 (2 H, m), 3.51-3.60 (2 H, m), 3.84 (3 H, s), 6.83-7.21 (3 H, m), 7.93 (1 H, d), 8.05 (3 H, d), 8.52 (3 H, d). |
| 7 | 4-Cl | 384 | d1 H-NMR (300 MHz, DMSO-d6) δ 1.69-1.93 (4 H, m), 2.46-2.60 (1 H, m), 2.75-2.98 (2 H, m), 3.47-3.59 (2 H, m), 7.20 (3 H, dd), 7.35 (2 H, d), 7.65 (2 H, d), 8.05 (1 H, d), 8.52 (1 H, d). |
| 8 | 3-tBu | 406 | d 1H-NMR (300 MHz, DMSO-d6) δ 1.27 (9 H, s), 1.66-1.95 (4 H, m), 2.51-2.60 (1 H, m), 2.83-2.98 (2 H, m), 3.47-3.60 (2 H, m), 7.06 (1 H, d), 7.22 (2 H, dd), 7.59 (3 H, d), 7.65 (3 H, s), 7.50 (2 H, d), 8.03 (1 H, d), 8.52 (1 H, d). |
| 9 | 2-NH2-4-CF3 | 433 | d1 H-NMR (300 MHz, DMSO-d6) δ 1.65-1.99 (4 H, m), 2.58-2.77 (1 H, m), 2.84-3.01 (2 H, m), 3.47-3.62 (2 H, m), 5.60 (2 H, s), 6.82 (1H, d), 7.19 (1 H, d), 7.21 (1 H, d), 7.63 (1 H, s), 8.05 (1 H, d), 8.52 (1 H, d). |
| 10 | 4-n-Pentyl | 420 | d.85-2.97 (2 H, m), 3.47-3.59 (2 H, m), 7.10 (2 H, d), 7.19 (1 H, dd), 7.50 (2 H, d), 8.05 (1 H, d), 8.52 (1 H, d). |
| 11 | 4-n-Octyl | 462 | d1 H-NMR (300 MHz, DMSO-d6) δ 0.85 (3 H, t), 1.25 (10 H, br), 1.52 (2 H, br), 1.69-1.95 (4 H, m), 2.46-2.60 (3 H, m), 2.85-2.98 (2 H, m), 3.47-3.59 (2 H, m), 7.09 (2 H, d), 7.19 (1 H, dd), 7.50 (2 H, d), 8.05 (1 H, d), 8.52 (1 H, d). |
| 12 | 4-Vinyl | 376 | d1 H-NMR (300 MHz, DMSO-d6) δ 1.69-1.95 (4 H, m), 2.46-2.60 (3 H, m), 2.85-2.98 (2 H, m), 3.47-3.61 (2 H, m), 5.16 (1 H, d), 5.72 (1 H, d), 6.66 (1 H, dd), 7.18 (1 H, d), 7.40 (2 H, d), 7.60 (2 H, s), 8.05 (1 H, d), 8.52 (1 H, d). |
| 13 | 3-CN | 375 | d1 H-NMR (300 MHz, DMSO-d6) δ 1.68-1.99 (4 H, m), 2.46-2.62 (1 H, m), 2.85-2.99 (2 H, m), 3.47-3.61 (2 H, m), 7.19 (1 H, d), 7.51 (1 H, d), 7.54 (1 H, d), 7.84 (1 H, d), 8.05 (1 H, d), 8.08 (1 H, s), 8.52 (1 H, d). |
| 14 | 3-NO2 | 395 | — |
| 15 | 3-Me-4-Br | 442 | d1 H-NMR (300 MHz, DMSO-d6) δ 1.68-1.97 (4 H, m), 2.31 (3 H, s), 2.46-2.61 (1 H, m), 2.85-2.99 (2 H, m), 3.47-3.61 (2 H, m), 7.18 (1 H, dd), 7.41 (1 H, dd), 7.47 (1 H, d), 7.63 (1 H, d), 8.05 (1 H, d), 8.08 (1 H, s), 8.52 (1 H, d). |

TABLE 1-continued

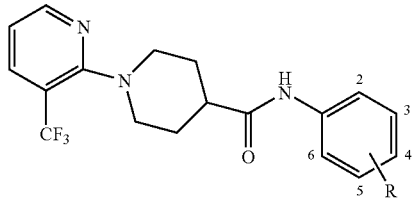

| Ex | R | [M + H]+ | NMR |
|---|---|---|---|
| 16 | 3-CF3-4-Br | 496 | d1 H-NMR (300 MHz, DMSO-d6) δ 1.68-1.97 (4 H, m), 2.46-2.61 (1 H, m), 2.85-2.99 (2 H, m), 3.47-3.61 (2 H, m), 7.19 (1 H, dd), 7.80 (2 H, br), 8.08 (1 H, d), 8.22 (1 H, B), 8.52 (1 H, d). |
| 17 | 4-NH2 | 365 | d1 H-NMR (300 MHz, DMSO-d6) δ 1.68-1.92 (4 H, m), 2.46-2.58 (1 H, m), 2.82-2.96 (2 H, m), 3.47-3.60 (2 H, m), 5.02 (2 H, s), 6.23 (1 H, dd), 6.70 (1 H, d), 6.87 (1 H, d), 6.94 (1 H, d), 7.18 (1 H, dd), 8.05 (1 H, d), 8.52 (1 H, d). |
| 18 | 4-Br | 428 | d1 H-NMR (300 MHz, DMSO-d6) δ 1.73-1.97 (4 H, m), 2.48-2.59 (1 H, m), 2.82-3.00 (2 H, m), 3.47-3.60 (2 H, m), 7.19 (1 H, dd), 7.47 (2 H, d), 7.61 (2 H, d), 8.05 (1 H, d), 8.52 (1 H, d). |
| 19 | 3-F | 368 | d1 H-NMR (300 MHz, DMSO-d6) δ 1.73-1.97 (4 H, m), 2.48-2.59 (1 H, m), 2.82-3.00 (2 H, m), 3.47-3.60 (2 H, m), 6.81-7.35 (1 H, m), 7.19 (1 H, dd), 7.33 (2 H, dd), 7.63 (1 H, d), 8.05 (1 H, d), 8.52 (1 H, |
| 20 | 3-Cl | 368 | d1 H-NMR (300 MHz, DMSO-d6) δ 1.73-1.97 (4 H, m), 2.48-2.59 (1 H, m), 2.82-3.00 (2 H, m), 3.47-3.60 (2 H, m), 7.08 (1 H, dd), 7.19 (1 H, dd), 7.34 (1 H, dd), 7.48 (1 H, d), 7.85 (1 H, d), 8.05 (1 H, d), 8.52 (1 H, d). |
| 21 | 4-I | 476 | d1 H-NMR (300 MHz, DMSO-d6) δ 1.73-1.97 (4 H, m), 2.48-2.59 (1 H, m), 2.82-3.00 (2 H, m), 3.47-3.60 (2 H, m), 7.08 (1 H, dd), 7.19 (1 H, dd), 7.47 (2 H, d), 7.63 (2 H, d), 7.85 (1 H, d), 8.05 (1 H, d), 8.52 (1 H, d). |
| 22 | 3-OH-4-OMe | 395 | d1 H-NMR (300 MHz, DMSO-d6) δ 1.73-1.94 (4 H, m), 2.45-2.56 (1 H, m), 2.82-2.97 (2 H, m), 3.47-3.60 (2 H, m), 3.72 (3 H, s), 6.81 (1 H, d), 6.96 (1 H, d), 7.19 (2 H, dd), 8.04 (1 H, d), 8.52 (1 H, d). |
| 23 | 3-NO2-4-Cl | 429 | d 1 H-NMR (300 MHz, DMSO-d6) δ 1.73-1.97 (4 H, m), 2.48-262 (1 H, m), 2.82-3.00 (2 H, m), 3.47-3.60 (2 H, m), 7.20 (1 H, dd), 7.71 (2 H, d), 7.81 (2 H, d), 8.05 (1 H, d), 8.52 (1 H, d). |
| 24 | 3-CF3-4-Cl | 452 | d 1 H-NMR (300 MHz, DMSO-d6) δ 1.73-1.99 (4 H, m), 2.48-262 (1 H, m), 2.82-3.00 (2 H, m), 3.47-3.60 (2 H, m), 7.19 (1 H, dd), 7.65 (1 H, d), 7.85 (1 H, d), 7.89 (1 H, d), 8.05 (1 H, d), 8.24 (1 H, d), 8.52 (1 H, d). |
| 25 | 3,4diCl | 419 | d 1 H-NMR (300 MHz, DMSO-d6) d1.68-1.97 (4 H, m), 2.53-2.62 (1 H, m), 2.86-3.00 (2 H, m), 3.47-3.61 (2 H, m), 7.19 (1 H, dd), 7.52 (1 H, d), 7.54 (1 H, d), 8.03 (1 H, d), 8.08 (1 H, d), 8.52 (1 H, d). |
| 26 | 3,4,5-triCl | 463 | d1 H-NMR (300 MHz, DMSO-d6) d1.67-1.96 (4 H, m), 2.49-2.60 (1 H, m), 2.83-3.00 (2 H, m), 3.47-3.61 (2 H, m), 7.19 (1 H, dd), 7.90 (2 H, s), 8.06 (1 H, d), 8.53 (1 H, d). |
| 27 | 3,5-diCl-4-OH | 435 | d1 H-NMR (300 MHz, DMSO-d6) d1.67-1.96 (4 H, m), 2.49-2.60 (1 H, m), 2.83-3.00 (2 H, m), 3.47-3.61 (2 H, m), 7.19 (1 H, dd), 7.64 (2 H, s), 8.06 (1 H, d), 8.53 (1 H, d). |
| 28 | 4-COOMe | 408 | d1 H-NMR (300 MHz, DMSO-d6) d1.67-1.98 (4 H, m), 2.53-2.64 (1 H, m), 2.83-3.02 (2 H, m), 3.47-3.61 (2 H, m), 3.82 (3 H, s), 7.19 (1 H, dd), 7.76 (2 H, d), 7.91 (2 H, d), 8.05 (1 H, dd), 8.53 (1 H, d). |
| 29 | 3-COOMe | 408 | d1 H-NMR (300 MHz, DMSO-d6) d1.67-1.98 (4 H, m), 2.51-2.62 (1 H, m), 2.83-3.02 (2 H, m), 3.47-3.61 (2 H, m), 3.86 (3 H, s), 7.19 (1 H, dd), 7.45 (1 H, dd), 7.63 (1 H, d), 7.84 (1 H, d), 8.05 (1 H, dd), 8.32 (1 H, d), 8.53 (1 H, d). |
| 30 | 3,5-diBr-4-OH | 522 | d1 H-NMR (300 MHz, DMSO-d6) d1.69-1.95 (4 H, m), 2.43-2.60 (1 H, m), 2.83-3.00 (2 H, m), 3.47-3.61 (2 H, m), 7.19 (1 H, dd), 7.83 (2 H, s), 8.06 (1 H, d), 8.53 (1 H, s). |
| 31 | 3-Cl-4-OH | 400 | d1 H-NMR (300 MHz, DMSO-d6) d1.69-1.95 (4 H, m), 2.43-2.60 (1 H, m), 2.83-3.00 (2 H, m), 3.47-3.61 (2 H, m), 6.89 (1 H, dd), 7.19 (1 H, dd), 7.27 (1 H, dd), 7.72 (1 H, s), 8.06 (1 H, d), 8.53 (1 H, d). |
| 32 | 3-CH2OH | 380 | d 1 H-NMR (300 MHz, DMSO-d6) d1.73-1.95 (4 H, m), 2.47-2.62 (1 H, m), 2.83-3.00 (2 H, m), 3.47-3.61 (2 H, m), 4.46 (2 H, dd), 5.18 (1 H, dd), 6.98 (1 H, d), 7.19 (1 H, dd), 7.23 (1 H, dd), 7.51 (1 H, d), 7.61 (1 H, s), 8.06 (1 H, d), 8.53 (1 H, d). |
| 33 | 4-CH2OH | 380 | d1 H-NMR (300 MHz, DMSO-d6) d1.73-1.95 (4 H, m), 2.49-2.62 (1 H, m), 2.83-3.00 (2 H, m), 3.47-3.61 (2 H, m), 4.43 (2 H, dd), 5.09 (1 H, dd), 6.98 (1 H, d), 7.19 (1 H, dd), 7.23 (2 H, d), 7.57 (2 H, d), 7.61 (1 H, s), 8.06 (1 H, d), 8.53 (1 H, d). |

TABLE 1-continued

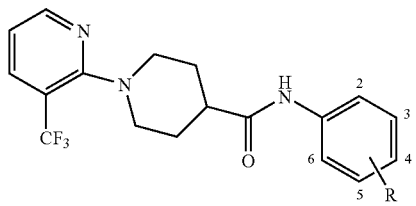

| Ex | R | [M + H]+ | NMR |
|----|---|----------|-----|
| 34 | 3-Me | 364 | d1 H-NMR (300 MHz, DMSO-d6) d1.77-1.94 (4 H, m), 2.49-2.61 (1 H, m), 2.83-3.00 (2 H, m), 3.33 (3 H, s), 3.47-3.61 (2 H, m), 6.83 (1 H, d), 7.11-7.23 (2 H, m), 7.42 (1 H, d), 7.47 (1 H, br), 8.06 (1 H, d), 8.53 (1 H, d). |

TABLE 2

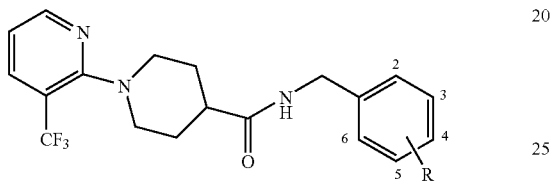

| Ex | R | [M + H]+ | NMR |
|----|---|----------|-----|
| 35 | 3-OH-4-OH | 396 | — |

TABLE 3

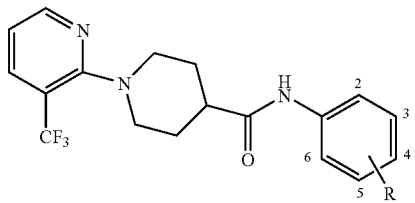

| Ex | R | [M + H]+ | NMR |
|----|---|----------|-----|
| 36 | 4-iPr | 392 | d 1 H-NMR (300 MHz, DMSO-d6) δ 1.14 (3 H, s), 1.16 (3 H, s), 1.67-1.81 (4 H, m), 2.46-2.56 (1 H, m), 2.75-2.98 (3 H, m), 3.47-3.59 (2 H, m), 7.13 (2 H, d), 7.18 (1 H, d), 7.49 (2 H, d), 8.03 (1 H, d), 8.51 (1 H, d), 9.83 (1 H, s). |
| 37 | 4-tBu | 372 | d 1 H-NMR (300 MHz, DMSO-d6) δ 1.23 (9 H, s), 1.67-1.86 (4 H, m), 2.43-2.56 (1 H, m), 2.75-2.88 (2 H, m), 3.66-3.83 (2 H, m), 6.97 (1 H, dd), 7.28 (2 H, d), 7.50 (2 H, d), 7.77 (1 H, dd), 8.19 (1 H, dd). |
| 38 | 4-Br | 394 | d1 H-NMR (300 MHz, DMSO-d6) δ 1.67-1.89 (4 H, m), 2.49-2.58 (1 H, m), 2.75-2.83 (2 H, m), 3.66-3.83 (2 H, m), 6.97 (1 H, dd), 7.47 (2 H, d), 7.61 (2 H, d), 7.78 (1 H, dd), 8.21 (1 H, dd). |
| 39 | 4-F | 334 | d1 H-NMR (300 MHz, DMSO-d6) δ 1.67-1.89 (4 H, m), 2.49-2.58 (1 H, m), 2.75-2.83 (2 H, m), 3.66-3.81 (2 H, m), 6.78-6.85 (1 H, m), 7.00 (1 H, dd), 7.33 (3 H, br), 7.63 (1 H, dd), 7.80 (1 H, dd), 8.21 (1 H, dd). |
| 40 | 4-Octyl | 429 | d1 H-NMR (300 MHz, DMSO-d6) δ 0.80-0.88 (3 H, m), 1.24 (12 H, br), 1.71 (2 H, br), 1.86 (4 H, br), 2.49-2.58 (1 H, m), 2.75-2.83 (2 H, m), 3.66-3.81 (2 H, m), 7.00 (1 H, dd), 7.09 (2 H, d), 7.50 (2 H, d), 7.79 (1 H, dd), 8.21 (1 H, dd). |

TABLE 4

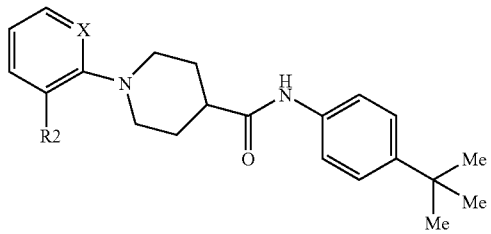

| Ex | X | R2 | [M + H]+ | NMR |
|---|---|---|---|---|
| 41 | CH | NO2 | 382 | d1 H-NMR (300 MHz, DMSO-d6) d 1.23 (9 H, m), 1.67-1.84 (4 H, m), 2.41-2.56 (1 H, m), 2.75-2.56 (2 H, m), 3.16-3.23 (2 H, m), 7.09 (1 H, dd), 7.25-7.36 (3 H, m), 7.44-7.61 (3 H, m), 7.78 (1 H, dd). |
| 42 | N | CN | 363 | — |

TABLE 5

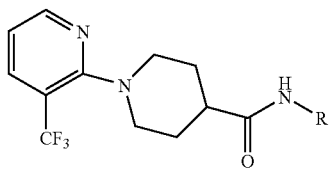

| Ex | R | salt | [M + H]+ | NMR |
|---|---|---|---|---|
| 43 | ![pyridine-CF3] | — | 419 | d1 H-NMR (300 MHz, DMSO-d6) d 1.68-1.97 (4 H, m), , 2.88-2.99 (3 H, m), 3.57-3.62 (2 H, m), 7.18 (1 H, dd), 8.05 (1 H. dd), 8.17 (1 H, dd), 8.29 (H, d), 8.52 (1 H, d), 8.72 (1 H, d). |
| 44 | ![isoquinoline] | — | 401 | d1 H-NMR (300 MHz, DMSO-d6) d 1.60-2.17 (4 H, m), 2.37-2.52 (1 H, m), 2.83-3.20 (2 H, m), 3.47-3.60 (2 H, m), 7.16 (1 H, dd), 7.64 (2 H, d), 7.81 (2 H, d), 8.04 (1 H, d), 8.51 (1 H, d). |
| 45 | ![benzoylphenyl] | — | 454 | d1 H-NMR (300 MHz, DMSO-d6) d1.67-1.99 (4 H, m), 2.57-2.63 (1 H. m), 2.84-2.96 (2 H, ml), 3.53-3.59 (2 H, m), 7.19 (1 H, dd), 7.53-7.81 (7 H, m), 8.05 (1 H, dd), 8.62 (1 H, dd). |
| 46 | ![benzothiazole-SH] | — | 439 | d1 H-NMR (300 MHz, DMSO-d6) d1.78-1.96 (4 H, m), 2.57-2.61 (1 H, m), 2.84-2.99 (2 H, m), 3.53-3.61 (2 H, m), 7.19 (1 H, dd), 7.25 (1 H, d), 7.53 (1 H, d), 8.04 (1 H, dd), 8.05 (1 H, dd), 8.53 (1 H, dd). |
| 47 | ![indazole] | — | 390 | d1 H-NMR (300 MHz, DMSO-d6) d1.78-1.96 (4 H, m), 2.57-2.63 (1 H, m), 2.84-3.02 (2 H, m), 3.53-3.62 (2 H, m), 7.12 (1 H, dd), 7.64 (1 H, d), 7.96 (1 H, ml), 8.05 (1 H, dd), 8.18 (1 H, s), 8.52 (1 H, dd). |
| 48 | ![ethyl-methoxy-phenoxy-ethylamine] | TFA | 453 | — |

TABLE 5-continued

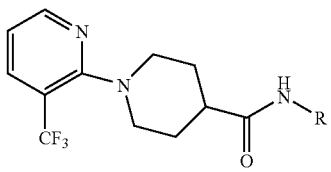

| Ex | R | salt | [M + H]+ | NMR |
|---|---|---|---|---|
| 49 | ![R group with N-H-S(=O)(=O)Me on methylphenyl] | — | 443 | — |
| 50 | ![5-methyl-2-CF3-pyridyl group] | — | 303 | 1 H-NMR (300 MHz, DMSO-d6) δ 3.87 (2 H, s), 5.04 (1 H, s), 3.92 (2 H, br), 6.73 (1 H, br), 7.16 (1 H, dd), 7.30 (2 H, d), 7.56 (2 H, d), 8.06 (1 H, dd), 8.50 (1 H, d). |

TABLE 6

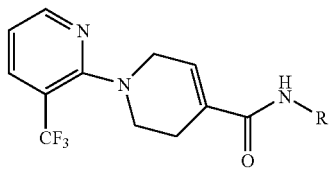

| Ex | R | salt | [M + H]+ | NMR |
|---|---|---|---|---|
| 51 |  | — | 404 | 1 H NMR (300 MHz, DMSO-d6) d 1.24 (9 H, s), 2.55 (2 H, br), 3.35 (2 H, dd), 3.95 (2 H, dd), 6.73 (1 H, br), 7.17 (1 H, dd), 7.30 (2 H, d), 7.55 (2 H, d), 8.06 (1 H, dd), 8.51 (1 H, d). |

Example 52

Synthesis of N-(2-bromophenyl)-4-(ethyl-3-methylanilino)butanamide

Step 1: 4-(ethyl-3-methylanilino)butyric acid ethyl ester

4-Bromobutyric acid ethyl ester (17.1 ml), potassium carbonate (20.5 g), and DMF (80 ml) were added to N-ethyl-m-toluidine (8 g), and the mixture was stirred at 95° C. for 17 hours. The reaction mixture was diluted with ethyl acetate, washed with water, and dried over magnesium sulfate. The solvent was evaporated, and the residue was purified by silica gel chromatography (hexane-ethyl acetate) to give the title compound (14.1 g).

MS (ESI) m/z: 250(M+H)+; 1H-NMR (300 MHz, CDCl3) δ 1.14 (3H, t), 1.26 (3H, t), 1.91 (2H, m), 2.27-2.37 (5H, m), 3.26-3.38 (4H, m), 4.14 (2H, q), 6.47-6.53 (3H, m), 7.07-7.12 (1H, m).

Step 2: 4-(ethyl-3-methylanilino)butyric acid

4N Solution (100 ml) of hydrogen chloride in dioxane and water (20 ml) was added to the compound (14.1 g) obtained in Step 1, and the mixture was stirred at 95° C. for 12 hours. The solvent was evaporated to give the title compound (13.7 g).

MS (ESI) m/z: 222 (M+H)+.

Step 3: N-(2-bromophenyl)-4-(ethyl-3-methylanilino)butanamide

1-Ethyl-3-(3-dimethylaminopropyl)carbodiimide hydrochloride (150 mg), 1-hydroxy-7-azabenzotriazole (106 mg), dichloromethane (2 ml), 2-bromoaniline (134 μl), and triethylamine (162 μl) were added to the compound (100 mg) obtained in Step 2, and the mixture was stirred at room temperature for 17 hours. The reaction mixture was diluted with ethyl acetate, washed with water, and dried over magnesium sulfate. The solvent was evaporated and the residue was purified by silica gel chromatography (hexane-ethyl acetate) to give the title compound (56 mg).

MS (ESI) m/z: 375 (M+H)+; 1H-NMR (300 MHz, CDCl3) δ 1.14 (3H, t, J=7.2 Hz), 2.03 (2H, m), 2.29 (3H, s), 2.47 (2H, t, J=7.2 Hz), 3.37 (4H, m), 6.51-6.58 (3H, m), 6.96 (1H, t, J=7.7 Hz), 7.11 (1H, t, J=8.2 Hz), 7.31 (1H, t, J=7.9 Hz), 7.52 (1H, d, J=8.1 Hz), 7.59 (1H, brs), 7.33 (1H, brd).

Synthesis of Examples 53-64

The compounds of Examples 53-64 shown in Tables 7-8 were synthesized in the same manner as in the Steps of Example 52 and using the corresponding amine instead of 2-bromoaniline of Example 52, Step 3. The final compound was purified by silica gel chromatography (hexane-ethyl acetate) or reversed phase high performance liquid chromatography (reversed phase HPLC) (water-acetonitrile, each containing 0.1% trifluoroacetic acid (TFA)).

TABLE 7

| Ex | R | salt | [M + H]+ | NMR |
|---|---|---|---|---|
| 52 | 2-Br | — | 375 | 1 H-NMR (300 MHz CDCl3) 1.14 (3 H, t, J = 7.2 Hz), 2.03 (2 H, m), 2.29 (3 H, s), 2.47 (2 H, t, J = 7.2 Hz), 3.37 (4 H, m), 6.51-6.58 (3 H, m), 6.95 (1 H, t, J = 7.7 Hz), 7.11 (1 H, t, J = 8.2 Hz). 7.31 (1 H, t, J = 7.9 Hz), 7.52 (1 H, d, J = 8.1 Hz), 7.59 (1 H, brs), 7.33 (1 H, brd) |
| 53 | 4-tBu | — | 353 | 1 H-NMR (300 MHz. CDCl3) 1.12 (3 H, t, J = 6.9 Hz), 1.29 (9 H, s), 1.99 (2 H, m), 2.29 (3 H, s), 2.38 (2 H, t, J = 7.1 Hz), 3.31-3.38 (4 H, m), 6.58 (3 H, m), 7.12 (1 H, t, J = 8.2 Hz), 7.29-7.40 (5 H, m) |
| 54 | 3-Br | TFA | 375 | — |
| 55 | 3-OCF3 | TFA | 381 | — |
| 56 | 4-F | TFA | 315 | — |
| 57 | 4-OMe | TFA | 327 | — |
| 58 | 3-F | TFA | 315 | 1 H-NMR (300 MHz. DMSO-d6) 1.03 (3H, t, J = 7.05 Hz), 1.72 (2 H, brs), 2.30 (3 H, s), 2.37 (2 H, t, J = 4.5 Hz), 3.47 (4 H, brs), 6.5-7.6 (4 H, br), 6.85 (1 H, td), 7.28-7.34 (2 H, m), 7.60 (1 H, d), 10.2 (1 H, s) |
| 59 | 3-OMe | TFA | 327 | — |

TABLE 8

| Ex | R | salt | [M + H]+ | NMR |
|---|---|---|---|---|
| 60 | (N-methyl-2,3-dihydro-1H-inden-5-amine) | TFA | 337 | — |
| 61 | (N-methylquinolin-8-amine) | 2TFA | 348 | — |
| 62 | (N-methylbenzo[d][1,3]dioxol-5-amine) | TFA | 341 | — |

TABLE 8-continued

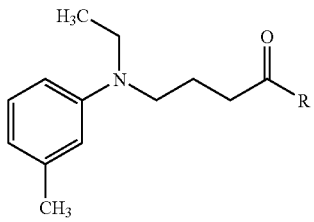

| Ex | R | salt | [M + H]+ | NMR |
|---|---|---|---|---|
| 63 | 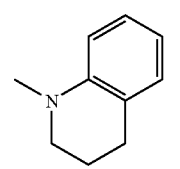 | TFA | 347 | 1 H-NMR (300 MHz DMSO-d6) 1.04 (3 H, t, J = 4.9 Hz). 1.81 (2 H, brs), 2.31 (3 H, s), 2.55 (2 H, t, J = 7.5 Hz), 3.52 (4 H, brd), 7.46-7.56 (3 H, m), 7.67 (1 H, d, J = 6.0 Hz), 7.76 (1 H, d, J = 6.0 Hz), 7.92-7.95 (1 H, m), 8.02-8.05 (1 H, m), 9.95 (1 H, s) |
| 64 | 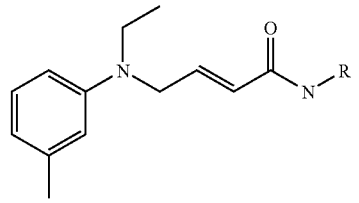 | TFA | 337 | 1 H-NMR (300 MHz, DMSO-d6) 1.00 (3 H, t, J = 7.2 Hz). 1.68 (2 H, brs), 1.84 (1 H, m), 2.30 (3 H, s), 2.50 (2 H, m), 2.67 (2 H, m), 3.42 (4 H, brd), 3.65 (2 H, t, J = 6.5 Hz), 6.70-7.70 (8 H, m) |

Synthesis of Examples 65-68

The compounds of Examples 65-68 shown in Table 9 were synthesized in the same manner as in Example 52.

TABLE 9

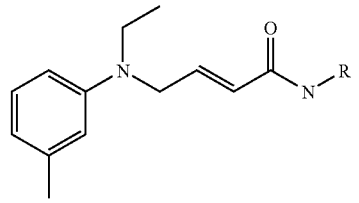

| Ex | R | salt | Dat |
|---|---|---|---|
| 65 | 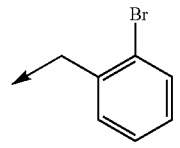 | TFA | MS (ESI) m/z: 392 (M + H)+; d1 H-NMR (300 MHz, DMSO-d6) d 1.08 (3 H, t), 2.23 (3 H, s), 2.82 (2 H, t), 3.25-3.45 (4 H, m), 4.02 (2 H, br), 5.85 (1 H, d), 5.90 (1 H, br), 6.40-6.65 (3 H, m), 7.08 (1 H, t), 7.31 (2 H, br), 7.55 (1 H, s), 8.10 (1 H, br). |
| 66 | 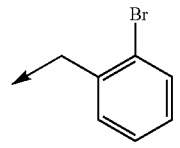 | TFA | MS (ESI) m/z: 388 (M + H)+; d1 H-NMR (300 MHz, DMSO-d6) d 1.09 (3 H, t), 2.26 (3 H, s), 3.39 (2 H, q), 4.10 (2 H, br), 4.33 (2 H, br), 6.10 (2 H, br), 6.55-6.70 (3 H, m), 7.10 (1 H, t), 7.15-7.25 (2 H, m), 7.35 (1 H, d), 7.60 (1 H, d), 8.55 (1 H, br). |
| 67 | 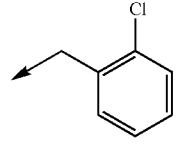 | TFA | MS (ESI) m/z: 343 (M + H)+; d1 H-NMR (300 MHz, DMSO-d6) d 1.09 (3 H, t), 2.24 (3 H, s), 3.38 (2 H, q), 4.09 (2 H, br), 4.36 (2 H, br), 6.10 (2 H, br), 6.50-6.70 (3 H, m), 7.10 (1 H, t), 7.27-7.41 (4 H, m), 8.50 (1 H, br). |

TABLE 9-continued

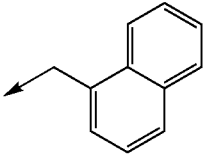

| Ex | R | salt | Dat |
|---|---|---|---|
| 68 | (1-naphthylmethyl) | TFA | MS (ESI) m/z: 359 (M + H)+; d1 H-NMR (300 MHz, DMSO-d6) d 1.07 (3 H, t), 2.22 (3 H, s), 3.36 (2 H, q), 4.10 (2 H, br), 4.77 (2 H, br), 6.00 (2 H, br), 6.50-6.70 (3 H, m), 7.10 (1 H, t), 7.40-7.60 (4 H, m), 7.85 (1 H, br), 7.90 (1 H, br), 8.10 (1 H, br), 8.55 (1 H, br). |

Synthesis of Examples 69-82

The compounds of Examples 69-82 shown in Table 10 were synthesized in the same manner as in Example 51.

The synthesis method of Example 51 is shown in detail in the following.

Example 51

Synthesis of 3'-trifluoromethyl-5,6-dihydro-2H-[1, 2']-bipyridinyl-4-carboxylic acid (4-tert-butylphenyl) amide

Step 1

Ethanol (38 ml) was added to 2-chloro-3-trifluoromethylpyridine (5 ml, 46 mmol), 1,4-dioxa-8-azaspiro[4.5]decane (8.3 ml, 65 mmol), and triethylamine (38 ml, 0.28 mol) and the mixture was kept sealed overnight at 160° C. The mixture was treated according to a conventional method using ethyl acetate as an extraction solvent to give an acetal intermediate (13 g).

Step 2 p-Toluenesulfonic acid monohydrate (0.2 g), acetone (80 ml), and water (20 ml) were added to acetal intermediate (10 g) obtained in Step 1, and the mixture was stirred overnight at 60° C. The mixture was treated according to a conventional method using ethyl acetate as an extraction solvent to give a crude product, whereby a ketone intermediate (8.2 g, 39 mmol) was obtained.

Step 3

The compound (8.2 g, 39 mmol) obtained in Step 2 was dissolved in diethyl ether (160 ml) and water (96 ml), and sodium cyanide (2.1 g, 43 mmol) and sodium hydrogen carbonate (6.6 g, 78 mmol) were added and the mixture was stirred overnight. The mixture was treated according to a conventional method using ethyl acetate as an extraction solvent to give a crude product, which was then purified by silica gel chromatography (hexane-ethyl acetate) to give a cyano intermediate (7.1 g, 30 mmol).

Step 4

A 50% (W/W) aqueous sulfuric acid solution (10 ml) was added to the cyano intermediate (7.1 g, 30 mmol) obtained in Step 3, and the mixture was stirred at 100° C. for 6 hours. The solution was neutralized and treated according to a conventional method using ethyl acetate as an extraction solvent. Ethanol (200 ml) and concentrated sulfuric acid (2 ml) were added to the obtained crude product, and the mixture was heated under reflux for 6 hours. The solution was neutralized and treated according to a conventional method using ethyl acetate as an extraction solvent. Pyridine (20 ml) and phosphorus oxychloride (1.8 ml) were added to the obtained crude product, and the mixture was stirred overnight. The mixture was treated according to a conventional method using ethyl acetate as an extraction solvent to give a crude product. Subsequently, the extract was purified by silica gel chromatography (hexane-ethyl acetate) to give an ester intermediate (3.1 g, 12 mmol).

Step 5: 3'-trifluoromethyl-5,6-dihydro-2H-[1,2']-bipyridinyl-4-carboxylic acid The ester intermediate (3.1 g, 12 mmol) obtained in Step 4 was dissolved in concentrated hydrochloric acid (25 ml), water (25 ml), and dioxane (50 ml), and the mixture was stirred at 100° C. for 3 hours. The solvent was evaporated to give a carboxylic acid intermediate.

Step 6: 3'-trifluoromethyl-5,6-dihydro-2H-[1,2']-bipyridinyl-4-carboxylic acid (4-tert-butylphenyl) amide The carboxylic acid (90 mg, 0.33 mmol) obtained in Step 5 was dissolved in thionyl chloride (12 ml), and the mixture was stirred at 70° C. for 2 hours. After evaporation of excess thionyl chloride, dichloromethane (2 ml), 4-tert-butylaniline (0.046 ml, 0.29 mmol), and triethylamine (0.071 ml, 0.51 mmol) were added, and the mixture was stirred for 2 hours. The solvent was evaporated to give a crude product. Then, the title compound was obtained by purification by reversed phase high performance liquid chromatography (reversed phase HPLC) (water-acetonitrile, each containing 0.1% trifluoroacetic acid (TFA)).

TABLE 10

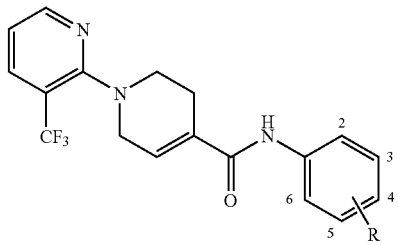

| Ex | R | Dat |
|---|---|---|
| 69 | 4-Me | MS (ESI) m/z: 362 (M + H)+ |
| 70 | 4-F | MS (ESI) m/z: 366 (M + H)+ |
| 71 | 4-CH=CH2 | MS (ESI) m/z: 374 (M + H)+ |
| 72 | 4-iPr | MS (ESI) m/z: 390 (M + H)+ |
| 73 | 4-I | MS (ESI) m/z: 474 (M + H)+ |
| 74 | 3,4-diF | MS (ESI) m/z: 384 (M + H)+ |
| 75 | 3-F-4-Cl | MS (ESI) m/z: 400 (M + H)+ |
| 76 | 4-CF3 | MS (ESI) m/z: 416 (M + H)+; 1 H-NMR (300 MHz, CDCl3) d 2.54 (2 H, m), 3.39 (2 H, t), 3.98 (2 H, dd), 6.81 (1 H, s), 7.15 (1 H, dd), 7.65 (2 H, d), 7.89 (2 H, d), 8.06 (1 H, dd), 8.50 (1 H, dd). |
| 77 | 4-SMe | MS (ESI) m/z: 394 (M + H)+ |
| 78 | 3,4,5-tri Cl | MS (ESI) m/z: 451 (M + H)+ |
| 79 | 3-F-4-OMe | MS (ESI) m/z: 396 (M + H)+ |
| 80 | 4-Et | MS (ESI) m/z: 376 (M + H)+ |
| 81 | 4-Cl | MS (ESI) m/z: 382 (M + H)+ |
| 82 | 3-F-4-Me | MS (ESI) m/z: 380 (M + H)+ |

Example 83

Synthesis of 3'-chloro-5,6-dihydro-2H-[1,2']-bipyridinyl-4-carboxylic acid (4-tert-butylphenyl)amide Step 1

Ethanol (53 ml) was added to 2,3-dichloropyridine (10 g, 68 mmol), 1,4-dioxa-8-azaspiro[4.5]decane (12 ml, 95 mmol), and triethylamine (53 ml, 0.41 mol), and the mixture was kept sealed overnight at 160° C. The mixture was treated according to a conventional method using ethyl acetate as an extraction solvent to give an acetal intermediate.

Step 2 p-Toluenesulfonic acid monohydrate (3.2 g, 17 mmol), acetone (100 ml), and water (20 ml) were added to the acetal intermediate obtained in Step 1, and the mixture was stirred overnight at 70° C. The mixture was treated according to a conventional method using ethyl acetate as an extraction solvent to give a crude product. The mixture was purified by recrystallization from methanol as a solvent to give a ketone intermediate (7.1 g, 34 mmol).

Step 3

A solution of lithium diisopropylamide (LDA) in tetrahydrofuran was prepared from tetrahydrofuran (60 ml), diisopropylamine (1.6 ml, 12 mmol), and n-butyllithium (1.6 mol/l n-hexane solution, 7.1 ml, 11 mmol) according to a conventional method. The compound (2.1 g, 10 mmol) obtained in Step 2 was dissolved in tetrahydrofuran (30 ml), and the solution was added to a solution of LDA prepared earlier, under an argon atmosphere at −78° C. The mixture was stirred at low temperature for 30 minutes, and a solution of 2-(N,N-bistrifluoromethylsulfonylamino)-5-chloropyridine (4.3 g, 11 mmol) in tetrahydrofuran (10 ml) was added, and the mixture was further stirred for 1 hour. The solvent was evaporated and the obtained crude product was purified by silica gel chromatography (hexane-ethyl acetate) to give an enol triflate intermediate (2.8 g, 8.2 mmol).

MS (ESI) m/z: 343 (M+H)+; 1H-NMR (300 MHz, CDCl3) δ 2.65 (2H, brs), 3.61 (2H, t, J=5.4 Hz), 4.05 (2H, brd, 2.7 Hz), 5.88 (1H, brs), 6.86 (1H, dd, J=7.5, 4.2 Hz), 7.61 (1H, d, J=7.5 Hz), 8.17 (1H, d, J=4.2 Hz).

Step 4

N,N-Dimethylformamide (130 ml) was added to the triflate intermediate (2.6 g, 7.7 mmol) obtained in Step 3, palladium acetate (0.10 g, 0.46 mmol), triphenylphosphine (0.24 g, 0.92 mmol), triethylamine (6.0 ml, 43 mmol), and ethanol (15 ml, 0.26 mol), and the mixture was stirred overnight under a carbon monoxide atmosphere. The mixture was treated according to a conventional method using ethyl acetate as an extraction solvent to give a crude product. The crude product was successively purified by silica gel chromatography (hexane-ethyl acetate) to give an ester intermediate (1.5 g, 5.6 mmol).

MS (ESI) m/z: 267 (M+H)+; 1H-NMR (300 MHz, CDCl3) δ 1.26 (3H, t, J=8.1 Hz), 2.59 (2H, m), 3.51 (2H, t, J=4.1 Hz), 4.08 (2H, m), 4.23 (2H, q, J=8.1 Hz), 6.84 (1H, dd, J=7.5, 4.1 Hz), 7.03 (1H, brs), 7.62 (1H, d, J=7.5 Hz), 8.20 (1H, d, J=4.1 Hz).

Step 5: 3'-chloro-5,6-dihydro-2H-[1,2']-bipyridinyl-4-carboxylic acid

The ester intermediate (1.5 g, 5.7 mmol) obtained in Step 4 was dissolved in concentrated hydrochloric acid (25 ml), water (25 ml), and dioxane (50 ml), and the mixture was stirred at 100° C. for 3 hours. The solvent was evaporated to give a carboxylic acid intermediate.

Step 6: 3'-chloro-5,6-dihydro-2H-[1,2']-bipyridinyl-4-carboxylic acid (4-tert-butylphenyl)amide The carboxylic acid (400 mg, 1.68 mmol) obtained in Step 5 was dissolved in thionyl chloride (12 ml), and the mixture was stirred at 70° C. for 2 hours. Excess thionyl chloride was evaporated, dichloromethane (12 ml), 4-tert-butylaniline (0.294 ml, 1.85 mmol), and triethylamine (0.469 ml, 3.36 mmol) were added, and the mixture was stirred for 2 hours. The solvent was evaporated to give a crude product. The crude product was successively purified by silica gel chromatography (hexane-ethyl acetate) to give the title compound (255 mg, 0.691 mmol).

MS (ESI) m/z: 370 (M+H)+; 1H-NMR (300 MHz, CDCl3) δ 1.28 (9H, s), 2.67 (2H, m), 3.54 (2H, t, J=5.7 Hz), 4.06 (2H, dd, J=6.0, 2.9 Hz), 6.75 (1H, m), 6.83 (1H, dd, J=7.8, 5.8 Hz), 7.34 (2H, d, J=9.6 Hz), 7.48 (1H, d, J=9.6 Hz), 7.60 (1H, dd, J=7.8, 1.7 Hz), 8.16 (1H, dd, J=5.8, 1.7 Hz).

Synthesis of Examples 84-96

The compounds of Examples 84-96 shown in Table 11 were synthesized in the same manner as in Example 83.

TABLE 11

| Ex | R | Dat |
|---|---|---|
| 84 | 4-CF3 | MS (ESI) m/z: 382 (M + H)+ |
| 85 | 4-I | MS (ESI) m/z: 440 (M + H)+ |
| 86 | 4-Br | MS (ESI) m/z: 392 (M + H)+ |
| 87 | 4-CO₂Me | MS (ESI) m/z: 372 (M + H)+ |
| 88 | 3-Me | MS (ESI) m/z: 328 (M + H)+ |
| 89 | 4-Cl | MS (ESI) m/z: 349 (M + H)+ |
| 90 | 4-CN | MS (ESI) m/z: 339 (M + H)+ |
| 91 | 4-SMe | MS (ESI) m/z: 360 (M + H)+ |
| 92 | 3-F-4-OMe | MS (ESI) m/z: 362 (M + H)+ |
| 93 | 4-Et | MS (ESI) m/z: 342 (M + H)+ |
| 94 | 3-CO2H | MS (ESI) m/z: 358 (M + H)+ |
| 95 | 3,4-diMe | MS (ESI) m/z: 342 (M + H)+ |
| 96 | 3-F-4-Me | MS (ESI) m/z: 346 (M + H)+ |

Synthesis of Examples 97-110

The compounds of Examples 97-101 shown in Table 12 were synthesized in the same manner as in Example 51, and the compounds of Examples 102-110 shown in Table 13 were synthesized in the same manner as in Example 83.

TABLE 12

| Ex | R1 | R2 | salt | Dat |
|---|---|---|---|---|
| 97 | CF3 | 2-pyridyl-5-I | TFA | MS (ESI) m/z: 475 (M + H)+ |
| 98 | CF3 | 2-Cl-4-pyridyl | TFA | MS (ESI) m/z: 383 (M + H)+ |
| 99 | CF3 | 4-t-Bu-cyclohexyl | — | MS (ESI) m/z: 410 (M + H)+ |
| 100 | CF3 | 6-Cl-3-pyridyl | TFA | MS (ESI) m/z: 383 (M + H)+ |
| 101 | CF3 | 5-CF3-2-pyridyl | TFA | MS (ESI) m/z: 417 (M + H)+ |

TABLE 13

| Ex | R1 | R2 | salt | Dat |
|---|---|---|---|---|
| 102 | Cl | 5-CF3-2-pyridyl | TFA | MS (ESI) m/z: 383 (M + H)+ |
| 103 | Cl | 5-Cl-2-pyridyl | TFA | MS (ESI) m/z: 350 (M + H)+ |

TABLE 13-continued

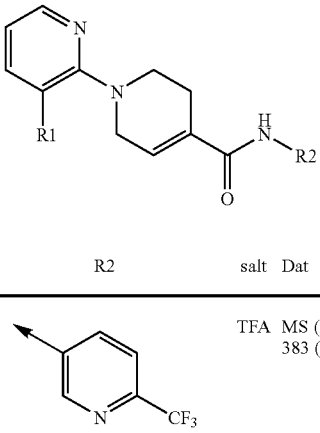

| Ex | R1 | R2 | salt | Dat |
|---|---|---|---|---|
| 104 | Cl | 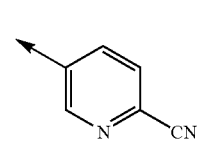 2-CF3-pyridin-5-yl | TFA | MS (ESI) m/z: 383 (M + H)+ |
| 105 | Cl | 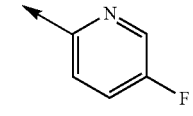 2-CN-pyridin-5-yl | TFA | MS (ESI) m/z: 340 (M + H)+ |
| 106 | Cl | 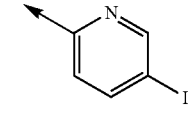 5-F-pyridin-2-yl | TFA | MS (ESI) m/z: 333 (M + H)+ |
| 107 | Cl | 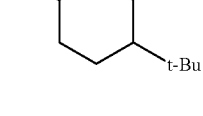 5-I-pyridin-2-yl | TFA | MS (ESI) m/z: 441 (M + H)+ |
| 108 | Cl | 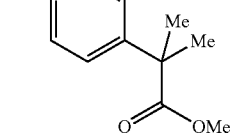 4-t-Bu-cyclohexyl | — | MS (ESI) m/z: 376 (M + H)+ |
| 109 | Cl | 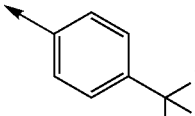 | — | MS (ESI) m/z: 414 (M + H)+ |
| 110 | Cl | 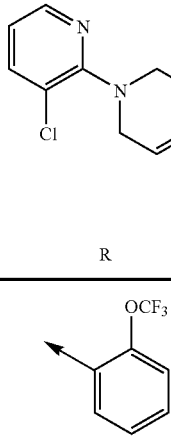 | — | MS (ESI) m/z: 387 (M + H)+ |

Synthesis of Examples 111-119

The compounds of Examples 111-119 shown in Table 14 were synthesized in the same manner as in Example 83.

TABLE 14

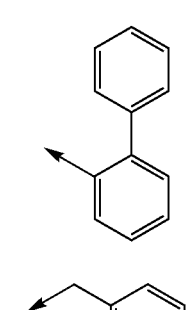

| Ex | R | salt | Dat |
|---|---|---|---|
| 111 | 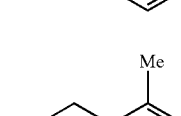 2-OCF3-phenyl | — | MS (ESI) m/z: 412 (M + H)+ |
| 112 | 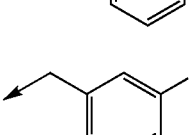 2-phenyl-phenyl | — | MS (ESI) m/z: 404 (M + H)+ |
| 113 |  phenyl | — | MS (ESI) m/z: 342 (M + H)+ |
| 114 |  2-Me-phenyl | — | MS (ESI) m/z: 356 (M + H)+ |
| 115 |  3-Br-phenyl | — | MS (ESI) m/z: 420 (M + H)+ |
| 116 | 4-F-phenyl | — | MS (ESI) m/z: 360 (M + H)+ |
| 117 | 4-Cl-phenyl | — | MS (ESI) m/z: 377 (M + H)+ |
| 118 | 4-OMe-phenyl | — | MS (ESI) m/z: 372 (M + H)+ |
| 119 | 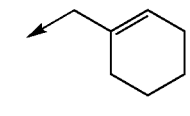 cyclohexenyl | — | MS (ESI) m/z: 346 (M + H)+ |

Example 120

6'-methoxy-3'-nitro-3,4,5,6-tetrahydro-2H-[1,2']-bipyridinyl-4-carboxylic acid (4-t-butylphenyl)amide

Step 1: piperidine-4-carboxylic acid-4-t-butylphenyl amide

Piperidine-1,4-dicarboxylic acid mono-t-butyl ester (10.6 g) was dissolved in dichloromethane (100 ml), 1-ethyl-3-(3-dimethylaminopropyl)carbodiimide hydrochloride (8.8 g), t-butylaniline (7.3 ml), and triethylamine (12.9 ml) were added, and the mixture was stirred overnight. The reaction mixture was diluted with ethyl acetate, washed with water, and dried over magnesium sulfate. The solvent was evaporated, a 4N solution (140 ml) of hydrogen chloride in dioxane and dioxane (60 ml) were added to the obtained residue, and the mixture was stirred at room temperature for 2 hours. The solvent was evaporated to give the title compound as a crude product.

Step 2: 6'-methoxy-3'-nitro-3,4,5,6-tetrahydro-2H-[1,2']-bipyridinyl-4-carboxylic acid (4-t-butylphenyl) amide The crude product (44 mg) obtained in Step 1 was dissolved in ethanol (2 ml), 2-chloro-3-nitro-6-methoxypyridine (34 mg) and triethylamine (125 μl) were added, and the mixture was kept sealed overnight. The solvent was evaporated, and the obtained crude product was purified by reversed phase high performance liquid chromatography (reversed phase HPLC) (water-acetonitrile, each containing 0.1% trifluoroacetic acid (TFA)) to give the title compound.

Examples 121-123 were synthesized as in Step 2 of Example 120 (the above-mentioned Example) and using the corresponding pyridine derivative. The final compound was purified by silica gel chromatography (hexane-ethyl acetate) or reversed phase high performance liquid chromatography (reversed phase HPLC) (water-acetonitrile, each containing 0.1% trifluoroacetic acid (TFA)).

The structure and physical data of Examples 120-123 are shown in Table 15.

TABLE 15

| Ex | R | Dat |
|---|---|---|
| 120 | 6-methoxy-3-nitropyridin-2-yl | MS (ESI) m/z: 413 (M + H)+ |
| 121 | 3-chloro-5-(ethoxycarbonyl)pyridin-2-yl | MS (ESI) m/z: 444 (M + H)+; 1 H-NMR (300 MHz, DMSO-d6) d1.67-1.99 (4 H, m), 2.57-2.63 (1 H, m), 2.84-2.96 (2 H, m), 3.53-3.59 (2 H, m), 7.19 (1 H, dd), 7.53-7.81 (7 H, m), 8.05 (1 H, dd), 8.52 (1 H, dd). |
| 122 | 3-chloro-4-carbamoylphenyl | MS (ESI) m/z: 415 (M + H)+ |
| 123 | pyridin-2-yl | MS (ESI) m/z: 338 (M + H)+ |

Experimental Example 1

Acetic Acid-Induced Writhing Method

The effect of the test compound was considered using male ICR mouse (4-week-old) according to a writhing test method induced by acetic acid. For intraperitoneal administration of a test compound and a standard product, the test compound was dissolved in a saline containing 5% DMSO and 5% Tween 80 to a suitable concentration. The test compound was administered 30 minutes before intraperitoneal administration of 0.8% acetic acid solution (diluted with saline), and the number of writhing was measured for 15 minutes from 5 minutes after acetic acid administration. A saline containing 5% DMSO and 5% Tween 80 was intraperitoneally administered to all control groups (vehicle administration group). Using indomethacin as a standard product, the same test was performed.

Figure 2:
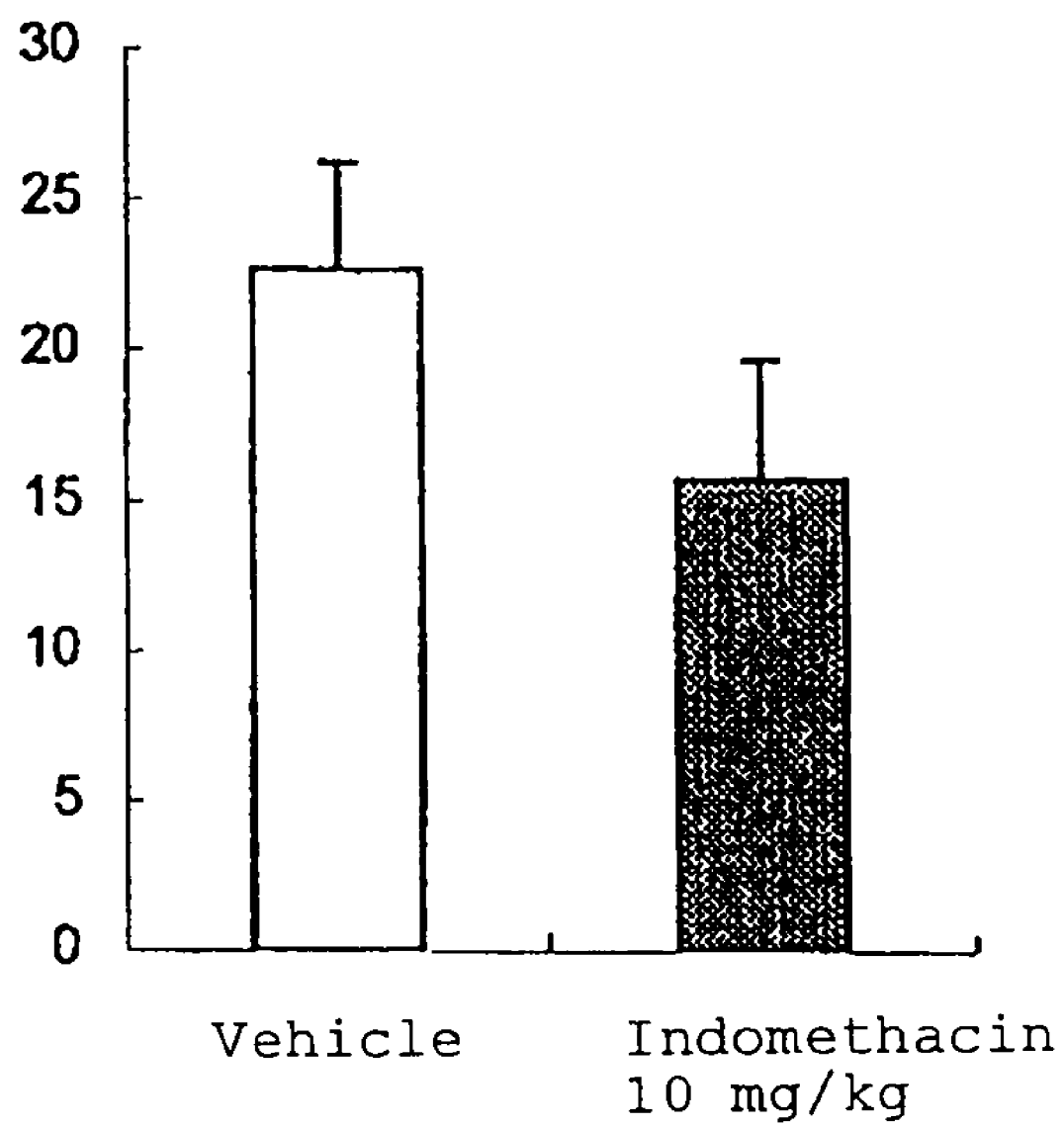
FIG. 2 is a graph showing the number of writhing for indomethacin by the acetic acid-induced writhing method.
Figure 3:
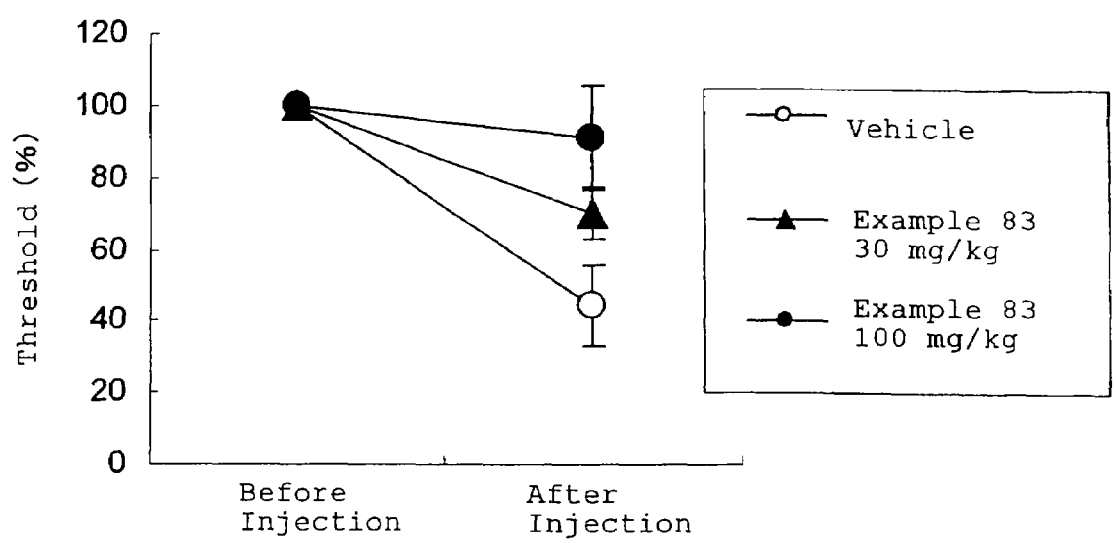
FIG. 3 is a graph showing the effect of the compound of the present invention (Example 83) by the mustard oil-induced thermal hyperalgesia model method.
Figure 4:
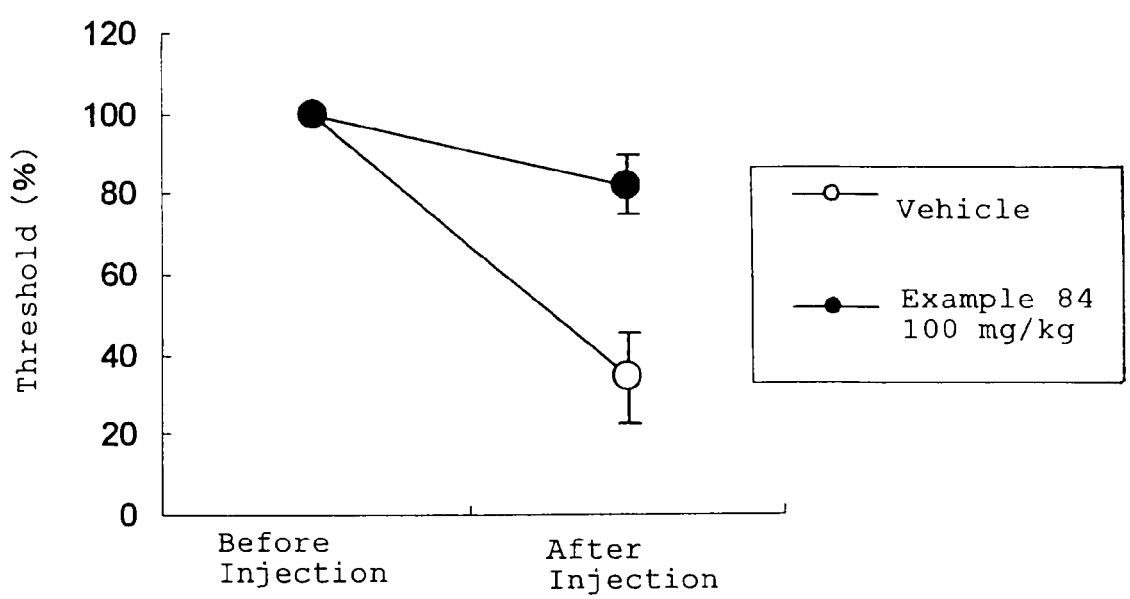
FIG. 4 is a graph showing the effect of the compound of the present invention (Example 84) by the mustard oil-induced thermal hyperalgesia model method.
Figure 5:
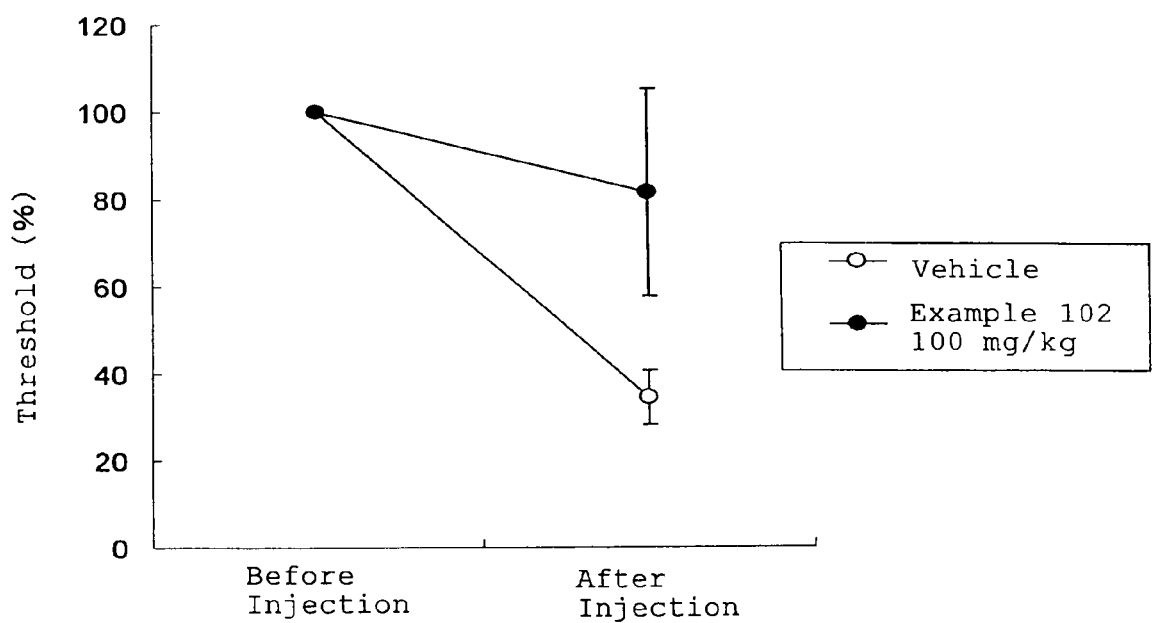
FIG. 5 is a graph showing the effect of the compound of the present invention (Example 102) by the mustard oil-induced thermal hyperalgesia model method.
Figure 6:
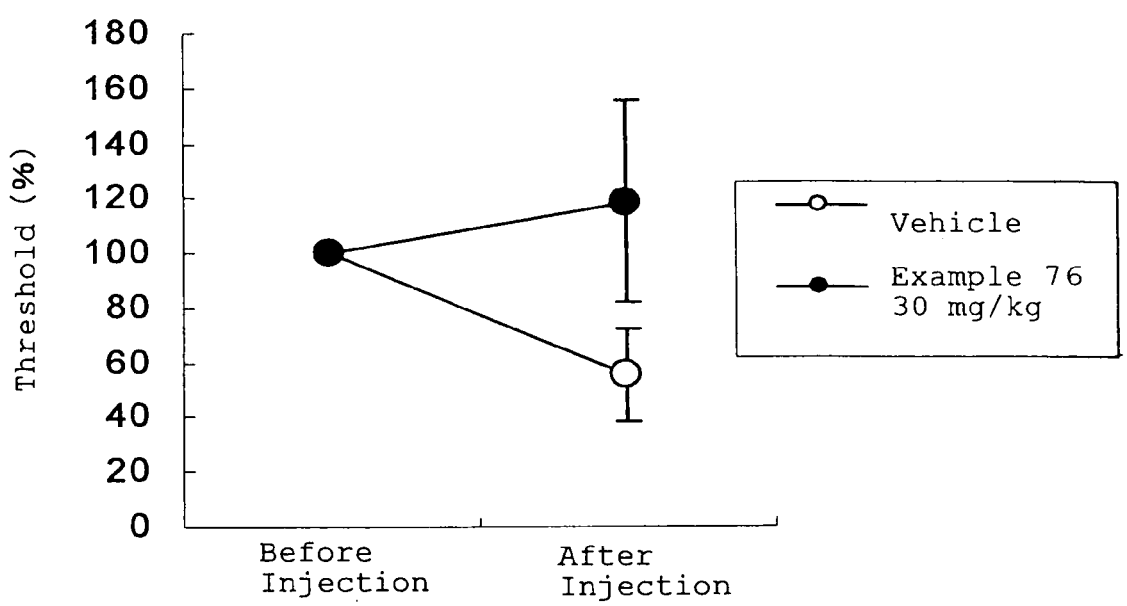
FIG. 6 is a graph showing the effect of the compound of the present invention (Example 76) by the mustard oil-induced thermal hyperalgesia model method.

The number of writhing by each test compound is shown in FIG. 1, and the number of writhings by indomethacin is shown in FIG. 2.

The number of writhing of each compound administration group to the number of writhing is shown in Table 16 as inhibition ratio.

TABLE 16

|  | Dose (mg/kg) | Inhibition ratio (%) |
| --- | --- | --- |
| Example 11 | 3 | 73 |
|  | 10 | 77 |
| Example 52 | 10 | 19 |
|  | 20 | 67 |
| Example 40 | 3 | 72 |
| indomethacin | 10 | 31 |

Experimental Example 2

Mustard Oil-Induced Thermal Hyperalgesia Model Method

Male ICR mouse was used. Mustard oil 10% (diluted with distilled water) was subcutaneously injected into both hind paws, and a hot plate test was performed 30 minutes later. The time from the instant the animal was placed on a hot plate to the occurrence of pain behavior was measured and used as an index. The compound was suspended in 0.5% CMC and orally administered at a dose of 5 ml/kg 1 hr before the hot plate test. The graph shows the calculated values relative to index measured before administration as 100%. The results are shown in FIGS. 3-6.

INDUSTRIAL APPLICABILITY

The present invention provides novel amide derivatives. The amide derivatives of the present invention have superior anti-inflammatory and analgesic activities and are a capsaicin-like active substance, or a substance that antagonizes a capsaicin action. Therefore, they are suitable as therapeutic agents for general pain treatments of headache, toothache, muscle pain, menstrual pain, wound pain, and the like, neuropathic pain associated with diabetic neuropathy, trigeminal neuropathy, herpes zoster, hyperalgesia and the like, or, inflammatory bowel diseases (Crohn's disease, ulcerative colitis, etc.), rheumatoid arthritis, osteoarthritis, Raynaud's disease, pruritus, allergic and nonallergic rhinitis, cystitis, frequent urination, incontinence, apoplexy, irritable bowel syndrome, respiratory diseases (asthma, chronic obstructive pulmonary disease etc.), dermatitis, gastric ulcer and duodenal ulcer, and useful for inflammatory bowel disease, frequent urination, incontinence, and asthma.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. An amide compound represented by the formula (I):

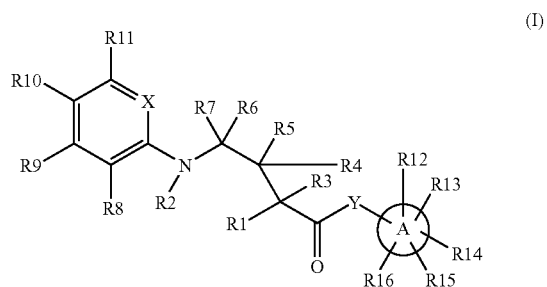

(I)

wherein:
A is a cycloalkyl group, an aryl group, or a heteroaryl group;
X is a nitrogen atom or CR17;
Y is —NRa-, —(CRbRb')m-, —NRa-(CRbRb')m-, —NRa-(CRbRb')m-O—, or —NRa'-(CRbRb')m-NRa-;
m is an integer of 0 to 4;
Ra, Ra', Rb, Rb', R1, R2, R3, R4, R5, R6, R7, R8, R9, R10, R11, R12, R13, R14, R15, R16, and R17 may be the same or different, and each is a hydrogen atom, a halogen atom, a cyano group, a nitro group, an ammonium group, an alkyl group optionally having one or more substituents, an alkenyl group optionally having one or more substituents, an alkynyl group optionally having one or more substituents, a cycloalkyl group optionally having one or more substituents (optionally having one or more hetero atoms in the ring), a cycloalkylalkyl group optionally having one or more substituents (optionally having one or more hetero atoms in the ring), an aryl group optionally having one or more substituents, an aralkyl group optionally having one or more substituents, a heteroaryl group optionally having one or more substituents, a heteroarylalkyl group optionally having one or more substituents, or -ZR18, wherein:
Z is —O—, —S(O)p—, —S(O)pO—, —NH—, —NR19-, —C(=O)—, —C(=O)O—, —C(=O)NH—, —C(=O)NR19-, —S(O)pNH—, —S(O)pNR19-, —NHC(=O)—, —NR19C(=O)—, —NHS(O)p-, or —NR19S(O)p-,
p is an integer of 0 to 2, and
R18 and R19 may be the same or different and each is a hydrogen atom, an alkyl group optionally having one or more substituents, an alkenyl group optionally having one or more substituents, an alkynyl group optionally having one or more substituents, a cycloalkyl group optionally having one or more substituents (optionally having one or more hetero atoms in the ring), a cycloalkylalkyl group optionally having one or more substituents (optionally having one or more hetero atoms in the ring), an aryl group optionally having one or more substituents, an aralkyl group optionally having one or more substituents, a heteroaryl group optionally having one or more substituents, a heteroarylalkyl group optionally having one or more substituents, or an acyl group, or R18 and R19 are optionally bonded to form a ring; or R3 and R4 are optionally bonded to form a carbon-carbon bond; or of R8, R9, R10, R11, R12, R13, R14, R15 and R16, those bonded to the adjacent carbon atom are optionally bonded to each other to form, together with the carbon atom constituting ring A, a saturated or unsaturated ring optionally having one or more hetero atoms in the ring formed; or when Y is —NRa-, Ra is optionally bonded to one of R12, R13, R14, R15, and R16 to form a ring together with the carbon atom constituting ring A, wherein R10 is other than an alkenyl group optionally having one or more substituents as defined above; or a pharmaceutically acceptable salt thereof.

2. The amide compound or pharmaceutically acceptable salt thereof of claim 1, wherein, in formula (I), A is any of a cycloalkyl group, a phenyl group, an isoquinolyl group, a pyridyl group, an indazolyl group, and a benzothiazolyl group.

3. An amide compound represented by the formula (IV):

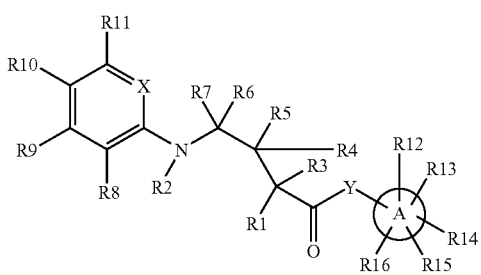

(IV)

wherein:
A is an aryl group or a heteroaryl group;
X is CR17;
Y is —NRa-;
Ra is a hydrogen atom or an alkyl group optionally having one or more substituents;
R2 is an alkyl group optionally having one or more substituents;
R1, R3, R4, R5, R6, R7, R8, R10, R11, and R17 are each a hydrogen atom;
R9 is an alkyl group optionally having one or more substituents; and
R12, R13, R14, R15, and R16 may be the same or different and each is a hydrogen atom, a halogen atom, an alkyl group optionally having one or more substituents, or -ZR18, wherein:
Z is —O—; and
R18 is an alkyl group optionally having one or more substituents, or
of R12, R13, R14, R15 and R16, those bonded to the adjacent carbon atom are optionally bonded to each other to form, together with the carbon atom constituting ring A, a saturated or unsaturated ring optionally having one or more hetero atoms in the ring formed, or
one of R12, R13, R14, R15, and R16 is optionally bonded to Ra to form a ring together with the carbon atom constituting ring A, or
a pharmaceutically acceptable salt thereof.

4. The amide compound or pharmaceutically acceptable salt thereof of claim 1, wherein, in formula (I):
A is a phenyl group, a quinolyl group, or a naphthyl group;
X is CH;
Y is —NH—; or the formula (V)

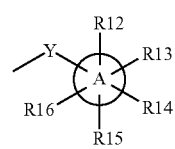

is the formula (VI)

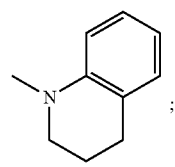

wherein:
R2 is an ethyl group;
R1, R3, R4, R5, R6, R7, R8, R10, R11, and R17 are each a hydrogen atom;
R9 is a methyl group;
R12, R13, R14, R15, and R16 may be the same or different and each is a hydrogen atom, a fluorine atom, a bromine atom, a trifluoromethoxy group, a methoxy group, or a t-butyl group; or
of R12, R13, R14, R15 and R16, those bonded to the adjacent carbon atom are optionally bonded to each other to form, together with the carbon atom constituting ring A, a saturated or unsaturated ring optionally having one or more hetero atoms in the ring formed.

5. A pharmaceutical composition, comprising an amide compound or pharmaceutically acceptable salt thereof of claim 1.

6. A pharmaceutical composition, comprising an amide compound or pharmaceutically acceptable salt thereof of claim 3.

7. A method of treating pain, comprising administering an effective amount of an amide compound or pharmaceutically acceptable salt thereof of claim 1 to a subject in need thereof.

8. A method of treating inflammatory bowel disease, comprising administering an effective amount of an amide compound or pharmaceutically acceptable salt thereof of claim 1 to a subject in need thereof.

9. A method of treating frequent urination or incontinence, comprising administering an effective amount of an amide compound or pharmaceutically acceptable salt thereof of claim 1 to a subject in need thereof.

10. A method of treating asthma, comprising administering an effective amount of an amide compound or pharmaceutically acceptable salt thereof of claim 1 to a subject in need thereof.

11. A package comprising a pharmaceutical composition, said pharmaceutical composition comprising an amide compound or pharmaceutically acceptable salt thereof of claim 1, and a written matter wherein said written matter explains use of said pharmaceutical composition.

12. A package comprising a pharmaceutical composition, said pharmaceutical composition comprising an amide compound or pharmaceutically acceptable salt thereof of claim 3, and a written matter wherein said written matter explains use of said pharmaceutical composition.

13. The amide compound or pharmaceutically acceptable salt thereof of claim 1, wherein Ra, Ra', Rb, Rb', R1, R2, R3, R4, R5, R6, R7, R8, R9, R10, R11, R12, R13, R14, R15, R16, and R17 may be the same or different, and each is a hydrogen atom, a halogen atom, a cyano group, a nitro group, an ammonium group, an alkyl group optionally having one or more substituents, an alkynyl group optionally having one or more substituents, a cycloalkyl group optionally having one or more substituents (optionally having one or more hetero atoms in the ring), a cycloalkylalkyl group optionally having one or more substituents (optionally having one or more hetero atoms in the ring), an aryl group optionally having one or more substituents, an aralkyl group optionally having one or more substituents, a heteroaryl group optionally having one or more substituents, a heteroarylalkyl group optionally having one or more substituents.

\* \* \* \* \*